(12) United States Patent
Slavin et al.

(10) Patent No.: US 9,783,781 B2
(45) Date of Patent: Oct. 10, 2017

(54) METHODS OF GENERATING OLIGODENDROCYTES AND CELL POPULATIONS COMPRISING SAME

(75) Inventors: Shimon Slavin, Tel-Aviv (IL); Chaya Brodie, Southfield, MI (US)

(73) Assignee: EXOSTEM BIOTEC LTD., Tel-Aviv (IL)

( * ) Notice: Subject to any disclaimer, the term of this patent is extended or adjusted under 35 U.S.C. 154(b) by 0 days.

(21) Appl. No.: 13/817,535

(22) PCT Filed: Aug. 14, 2011

(86) PCT No.: PCT/IL2011/000660
§ 371 (c)(1),
(2), (4) Date: Feb. 19, 2013

(87) PCT Pub. No.: WO2012/023132
PCT Pub. Date: Feb. 23, 2012

(65) Prior Publication Data
US 2013/0149288 A1    Jun. 13, 2013

Related U.S. Application Data

(60) Provisional application No. 61/373,909, filed on Aug. 16, 2010, provisional application No. 61/433,301, filed on Jan. 17, 2011.

(51) Int. Cl.
*C12N 15/113* (2010.01)
*A61K 35/12* (2015.01)
*C12N 5/079* (2010.01)

(52) U.S. Cl.
CPC .......... *C12N 5/0622* (2013.01); *C12N 15/113* (2013.01); *A61K 35/12* (2013.01); *C12N 2310/141* (2013.01); *C12N 2320/30* (2013.01); *C12N 2330/10* (2013.01); *C12N 2500/25* (2013.01); *C12N 2501/39* (2013.01); *C12N 2501/65* (2013.01); *C12N 2506/025* (2013.01); *C12N 2506/1353* (2013.01); *C12N 2506/1384* (2013.01); *C12N 2506/1392* (2013.01)

(58) Field of Classification Search
None
See application file for complete search history.

(56) References Cited

U.S. PATENT DOCUMENTS

| 2008/0171715 | A1 | 7/2008 | Brown et al. |
| 2008/0176328 | A1 | 7/2008 | Chang et al. |
| 2008/0206256 | A1 | 8/2008 | Spong et al. |
| 2008/0241115 | A1 | 10/2008 | Suh et al. |
| 2009/0010895 | A1 | 1/2009 | Offen et al. |
| 2010/0003751 | A1 | 1/2010 | Revel et al. |
| 2010/0021434 | A1 | 1/2010 | Melamed et al. |
| 2010/0150947 | A1 | 6/2010 | Siemionow |
| 2011/0311984 | A1 | 12/2011 | Paek et al. |
| 2015/0024966 | A1 | 1/2015 | Brodie et al. |
| 2015/0037298 | A1 | 2/2015 | Brodie et al. |
| 2015/0037299 | A1 | 2/2015 | Brodie et al. |

FOREIGN PATENT DOCUMENTS

| EP | 1506997 | 2/2005 |
| EP | 1705245 | 9/2006 |
| WO | WO 2006/134602 | 12/2006 |
| WO | WO 2009/023525 | 2/2009 |
| WO | WO 2009/122413 | 10/2009 |
| WO | WO 2009/144718 | 12/2009 |
| WO | WO 2010/111522 | 9/2010 |
| WO | WO 2010/144698 | 12/2010 |
| WO | WO 2011/030336 | 3/2011 |
| WO | WO 2011/159075 | 12/2011 |
| WO | WO 2012/023132 | 2/2012 |
| WO | WO 2013/124815 | 8/2013 |
| WO | WO 2013/124816 | 8/2013 |
| WO | WO 2013/124817 | 8/2013 |

OTHER PUBLICATIONS

Riggi et al., EWS-FLI-1 modulates miRNA145 and SOX2 expression to initiate mesenchymal stem cell reprogramming toward Ewing sarcoma cancer stem cells. Genes & Development. 2010, 24:916-932.*
Silber et al., miR-124 and miR-137 inhibit proliferation of glioblastoma multiforme cells and induce differentiation of brain tumor stem cells. BMC Medicine;2008, vol. 6, Special section p. 1-17.*
Kosztowski et al., Applications of neural and mesenchymal stem cells in the treatment of gliomas. Expert Rev Anticancer Ther. May 2009;9(5):597-612.*
Sasportas et al., Assessment of therapeutic efficacy and fate of engineered human mesenchymal stem cells for cancer therapy. p. 4322-4327. PNAS, 2009, vol. 106.*
Nakamizo et al., Human Bone Marrow-Derived Mesenchymal Stem Cells in the Treatment of Gliomas. Cancer Res, 2005, 65:3307-3318.*
Phillips et al., Genetic Modification of Stem Cells for Transplantation. Adv Drug Deliv Rev. Jan. 14, 2008; 60(2): 160-172.*
Yuan et al., Transfer of MicroRNAs by Embryonic Stem Cell Microvesicles. PloS ONE 4(3), e4722, pp. 1-8.*

(Continued)

*Primary Examiner* — Scott Long
*Assistant Examiner* — Arthur S Leonard
(74) *Attorney, Agent, or Firm* — The Roy Gross Law Firm, LLC; Roy Gross

(57) ABSTRACT

A method of generating a population of cells useful for treating a brain disorder in a subject is disclosed. The method comprises contacting mesenchymal stem cells (MSCs) with at least one exogenous miRNA having a nucleic acid sequence at least 90% identical to a sequence selected from the group consisting of SEQ ID NOs: 15-19 and 27-35, thereby generating the population of cells and/or generating neurotrophic factors that may provide important signals to damaged tissues or locally residing stem cells. MSCs differentiated by miRs may also secrete miRs and deliver them to adjacent cells and therefore provide important signals to neighboring endogenous normal or malignant cells.

4 Claims, 21 Drawing Sheets
(19 of 21 Drawing Sheet(s) Filed in Color)

(56) References Cited

OTHER PUBLICATIONS

International Search Report and the Written Opinion Dated Dec. 28, 2011 From the International Searching Authority Re. Application No. PCT/IL2011/000660.

Lakshmipathy et al. "Concise Review: MicroRNA Expression in Multipotent Mesenchymal Stromal Cells", Stem Cells, 26: 356-363, 2008. p. 356, Abstract, p. 357, Left col., Para 5, p. 358, Right col., Para 2, p. 358, Table 2, p. 359, Left col., Para 4, p. 360, Right col., Para 2.

Liu et al. "Induction of Oligodendrocyte Differentiation by Olig2 and Sox10: Evidence for Reciprocal Interactions and Dosage-Dependent Mechanisms", Developmental Biology, 302: 683-693, 2007.

Luo et al. "Connective Tissue Growth Factor (CTGF) Is Regulated by Wnt and Bone Morphogenetic Proteins Signaling in Osteoblast Differentiation of Mesenchymal Stem Cells", The Journal of Biological Chemistry, 279(53): 55958-55968, Dec. 31, 2004. p. 55958, Abstract, p. 55967, Fig.7.

Song et al. "Connective Tissue Growth Factor (CTGF) Acts as a Downstream Mediator of TGF-Beta1 to Induce Mesenchymal Cell Condensation", Journal of Cellular Physiology, 210: 398-410, 2007. p. 398, Abstract, p. 399, Left col. Para 2, p. 402, Fig.2, p. 405, Right col., Para 1.

International Preliminary Report on Patentability Dated Feb. 28, 2013 From the International Bureau of WIPO Re. Application No. PCT/IL2011/000660.

International Search Report and the Written Opinion Dated Oct. 10, 2013 From the International Searching Authority Re. Application No. PCt/IB2013/051429.

International Search Report and the Written Opinion Dated Oct. 10, 2013 From the International Searching Authority Re. Application No. PCT/IB2013/051430.

Communication Pursuant to Rule 70(2) and 70a(2) EPC Dated Jan. 9, 2014 from the European Patent Office Re. Application No. 11817858.1.

Supplementary European Search Report and the European Search Opinion Dated Dec. 17, 2013 from the European Patent Office Re. Application No. 11817858.1.

Letzen et al. "MicroRNA Expression Profiling of Oligodendrocyte Differentiation from Human Embryonic Stem Cells", PLoS One, XP055091734, 5(5): e-10480-1-e10480-12, May 2010. p. 2, col. 2, Para 2, Fig.2, Table 1.

Zhao et al. "MicroRNA-Mediated Control of Oligodendrocyte Differentiation", Neuron, XP055091729, 65(5): 612-626, Mar. 11, 2010. p. 613, col. 2, Para 2, Figs.3, 4.

Communication Relating to the Results of the Partial International Search Dated Aug. 12, 2013 From the International Searching Authority Re. Application No. PCT/IB2013/051430.

Communication Relating to the Results of the Partial International Search Dated Aug. 14, 2013 from the International Searching Authority Re. Application No. PCT/IB2013/051429.

International Search Report and the Written Opinion Dated Aug. 21, 2013 From the International Searching Authority Re. Application No. PCT/IB2013/051428.

Akerblom et al. "Functional Studies of MicroRNAs in Neural Stem Cells: Problems and Perspectives", Frontiers in Neuroscience, XP055074176, 6(Art.14): 1-10, Feb. 2012.

Gao "Context-Dependent Functions of Specific MicroRNAs in Neuronal Development", Neuronal Development, XP021081673, 5(25): 1-9, Oct. 2010.

Gong et al. "Immortalized Mesenchymal Stem Cells: An Alternative to Primary Mesenchymal Stem Cells in Neuronal Differentiation and Neurogeneration Associated Studies", Journal of Biomedical Science, XP021111456, 18(87): 1-16, Nov. 25, 2011.

Kang et al. "Kaposi's Sarcoma-Associated Herpesvirus ORF57 Promotes Escape of Viarl and Human Interleukin-6 From MicroRNA-Mediated Suppression", Journal of Virology, XP055073965, 85(6): 2620-2630, Mar. 2011.

Karaoz et al. "Human Dental Pulp Stem Cells Demonstrate Better Neural and Epithelial Stem Cell Properties Than Bone Marrow-Derived Mesenchymal Stem Cells", Histochemistry and Cell Biology, XP055074788, 136(4): 455-473, Oct. 31, 2011.

Katsushima et al. "Contribution of MicroRNA-1275 to Claudin 11 Protein Suppression Via A Polycomb-Mediated Silencing Mechanism in Human Glioma Stem-Like Cells", The Journal of Biological Chemistry, XP055074166, 287(33): 27396-27406, Aug. 10, 2012.

Kim et al. "A Development Taxonomy of Gliobastoma Defined and Maintained by MicroRNAs", Cancer Research, XP055073956, 71(9): 3387-3399, May 2011.

Liu et al. "MicroRNAs Regulation Modulated Self-Renewal and Lineage Differentiation of Stem Cells", Cell Transplantation, XP002605501, 18(9): 1039-1045, Jan. 2009.

Maisel et al. "Genome-Wide Expression Profiling and Functional Network Analysis Upon Neuroectodermal Conversion of Human Mesenchymal Stem Cells Suggest HIF-1 and MiR-124a as Important Regulators", Experimental Cell Research, XP055074156, 316(17): 2760-2778, Oct. 2010.

Ozata et al. "The Role of MicroRNA Deregulation in the Pathogenesis of Adrenocortical Carcinoma", Endocrine-Related Cancer, XP055074162, 18(6): 643-655, Oct. 27, 2011.

Shookhoff et al. "The Emerging Role of MicroRNAs in Adult Stem Cells", Adult Stem Cells: Biology and Methods of Analysis, XP008163996, Chap.3: 57-97, 2011.

Xin et al. "Exosome-Mediated Transfer of MiR-133b From Multipotent Mesenchymal Stromal Cells to Neural Cells Contributes to Neurite Outgrowth", Stem Cells, XP055073957, 30(7): 1556-1564, Jul. 18, 2012.

Zhang et al. "Isolation and Characterization of Mesenchymal Stem Cells Derived from Bone Marrow Patients With Parkinson's Disease", In Vitro Cellular & Developmental Biology—Animal, XP055074787, 44(5-6): 169-177, Jun. 2008.

Development Biology—Animal, XP055074787, 44(5-6): 169-177, Jun. 2008.

Search Report and Written Opinion Dated Dec. 13, 2013 from the Intellectual Property Office of Singapore Issued by the Danish Patent and Trademark Office Re. Application No. 201301101-0.

International Preliminary Report on Patentability Dated Sep. 4, 2014 from the International Bureau of WIPO Re. Application No. PCT/IB2013/051430.

International Preliminary Report on Patentability Dated Sep. 4, 2014 from the International Bureau of WIPO Re. Application No. PCT/IB2013/051428.

International Preliminary Report on Patentability Dated Sep. 4, 2014 from the International Bureau of WIPO Re. Application No. PCT/IB2013/051429.

Restriction Official Action Dated May 22, 2015 from the US Patent and Trademark Office Re. U.S. Appl. No. 14/380,155.

Restriction Official Action Dated May 13, 2015 From the US Patent and Trademark Office Re. U.S. Appl. No. 14/380,165.

Communication Pursuant to Article 94(3) EPC Dated Mar. 3, 2015 from the European Patent Office Re. Application No. 11817858.1.

* cited by examiner

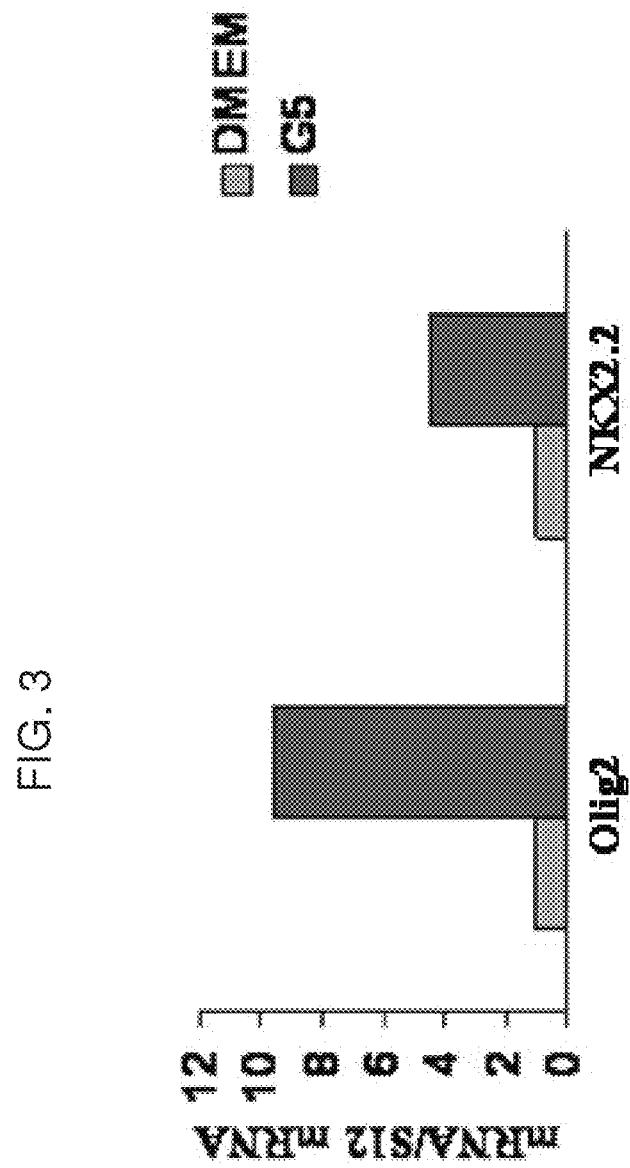

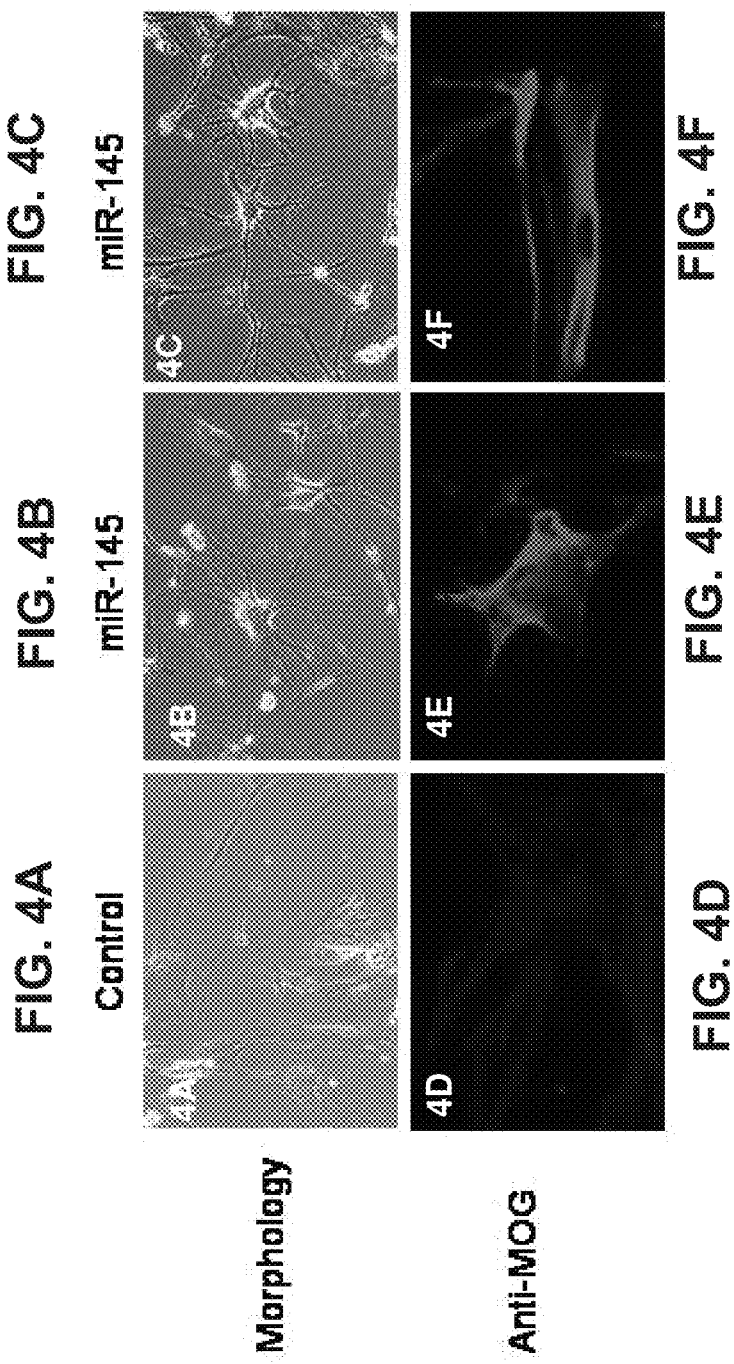

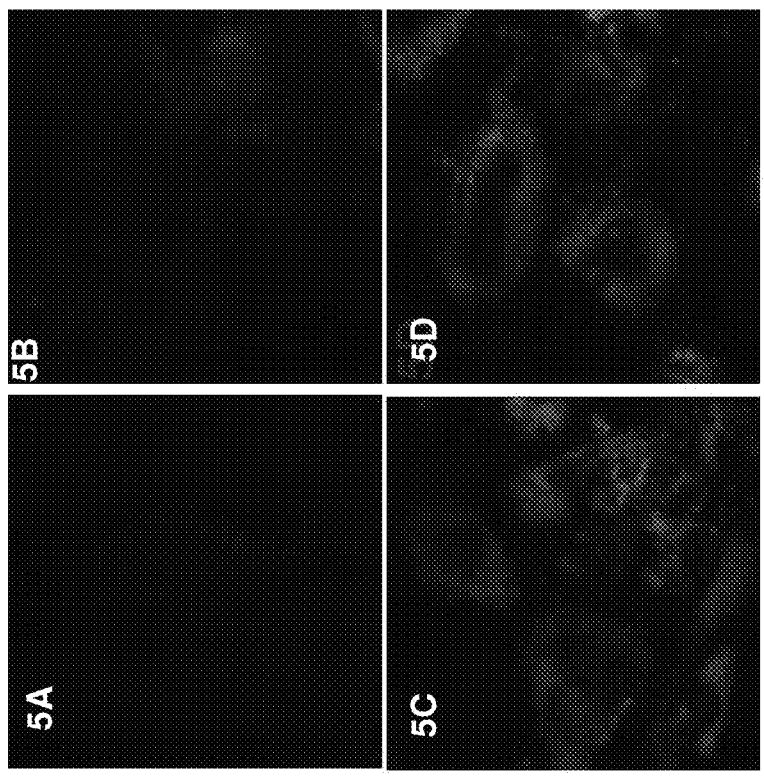

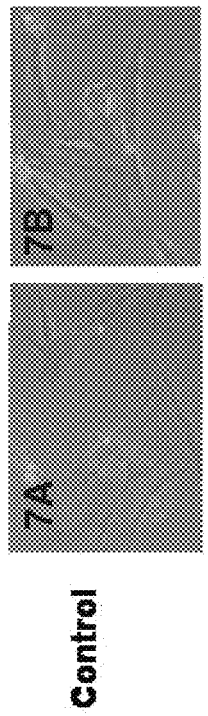
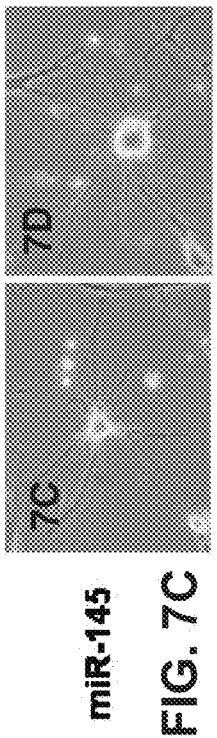
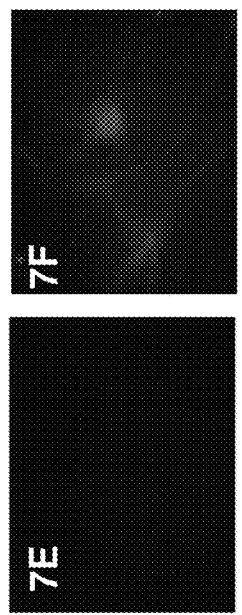
FIG. 7A  FIG. 7B  FIG. 7C  FIG. 7D  FIG. 7E  FIG. 7F
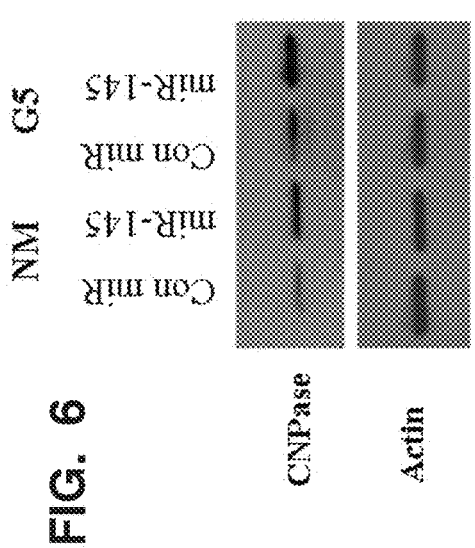
FIG. 6

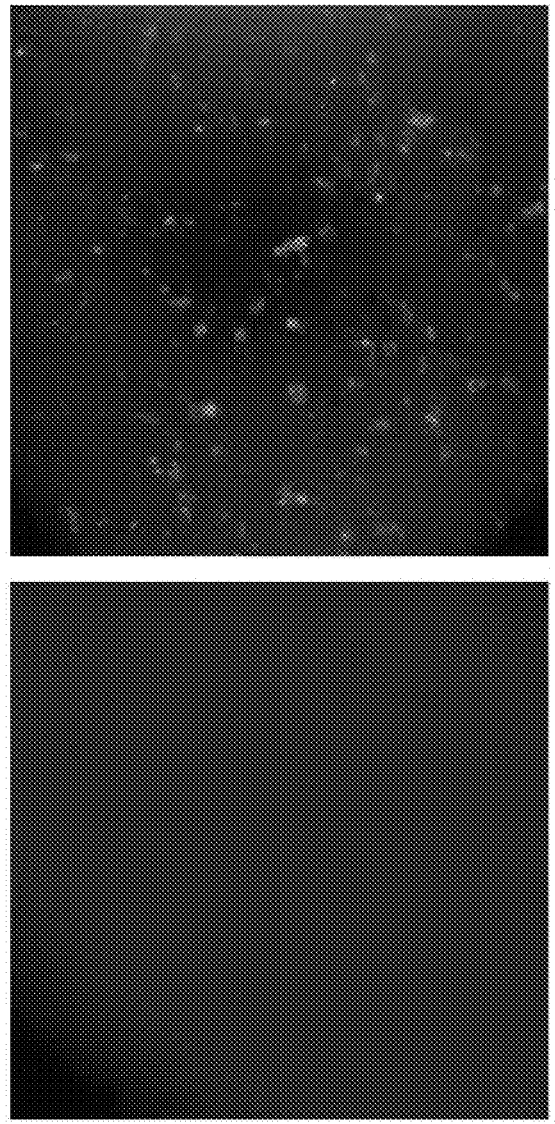

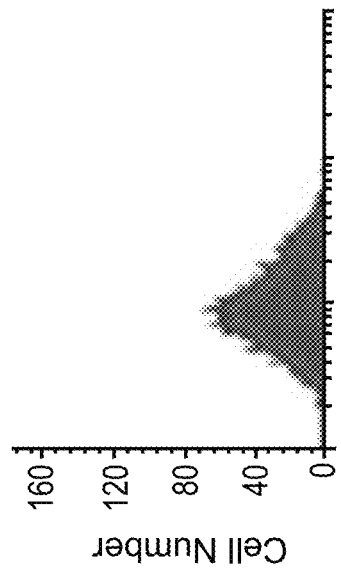
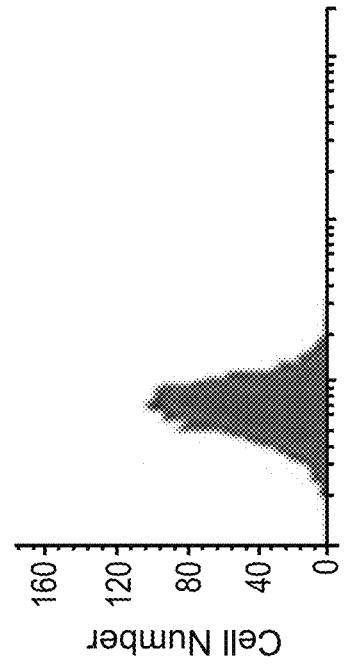
FIG. 10A Con miR
FIG. 10B miR-145

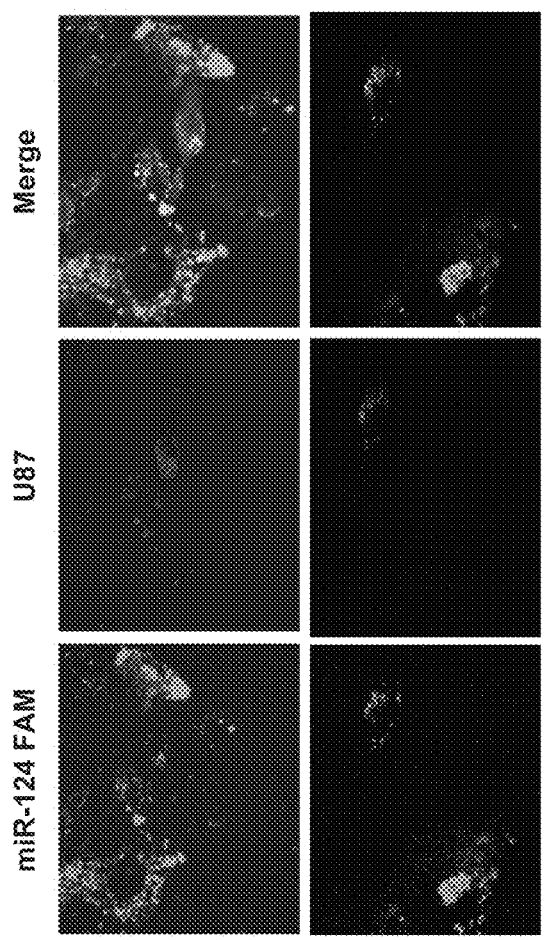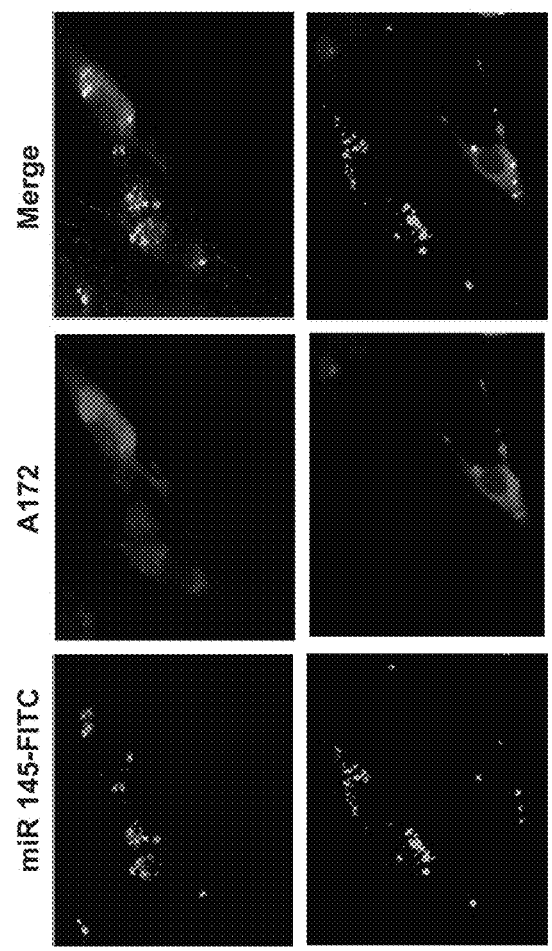

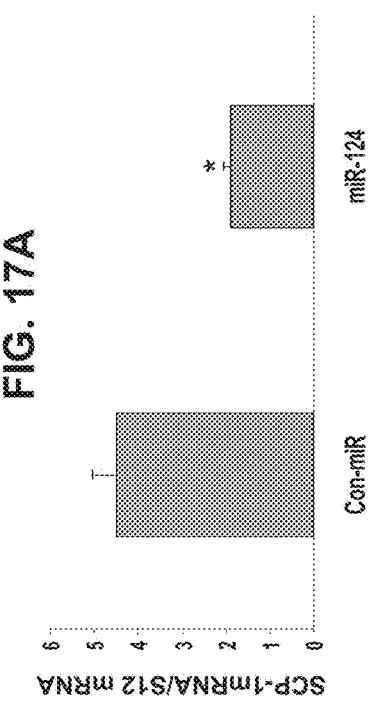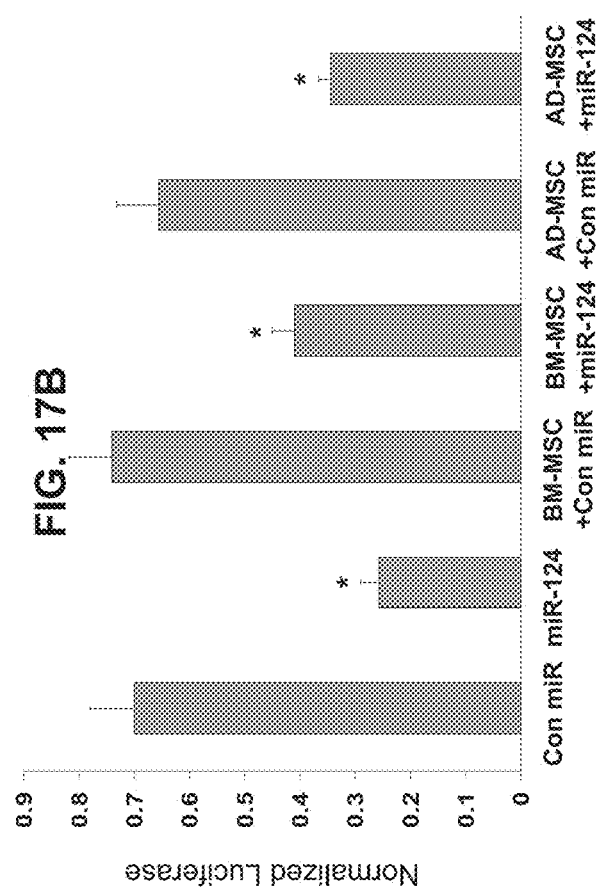

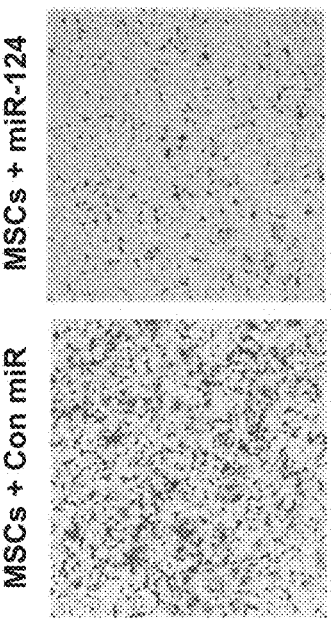
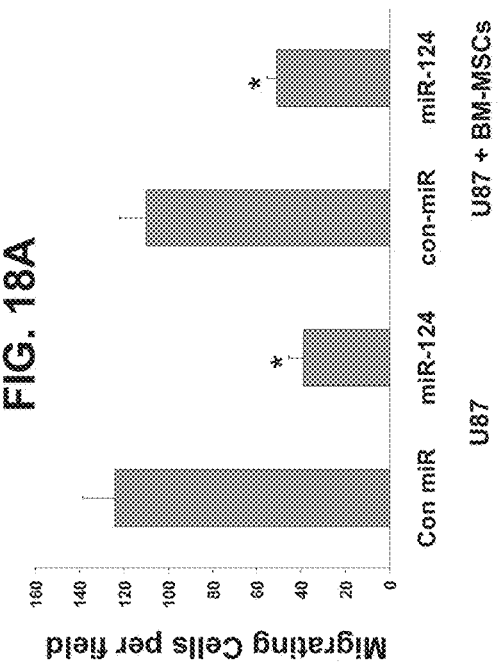
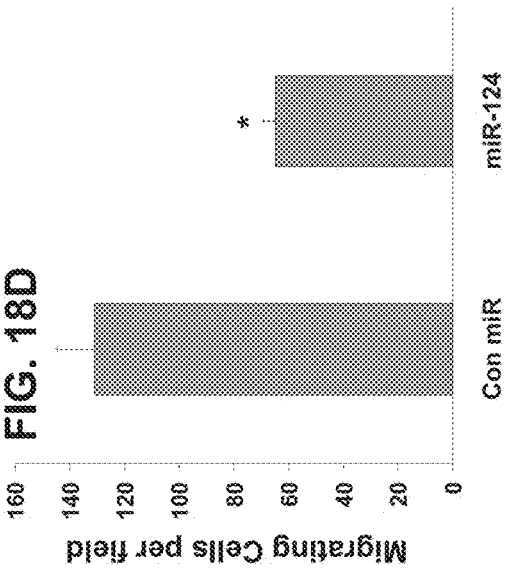
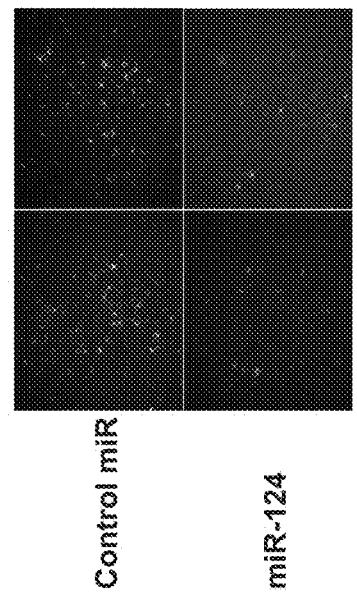

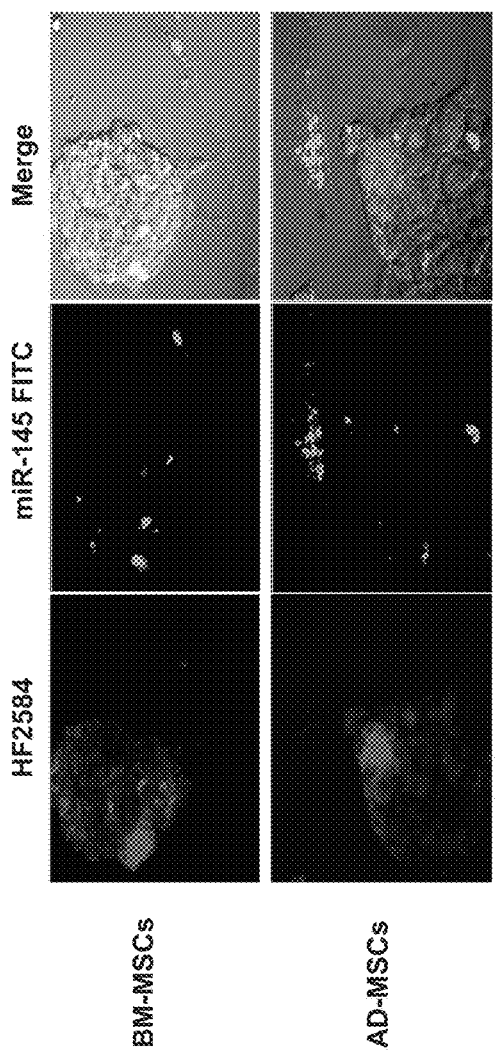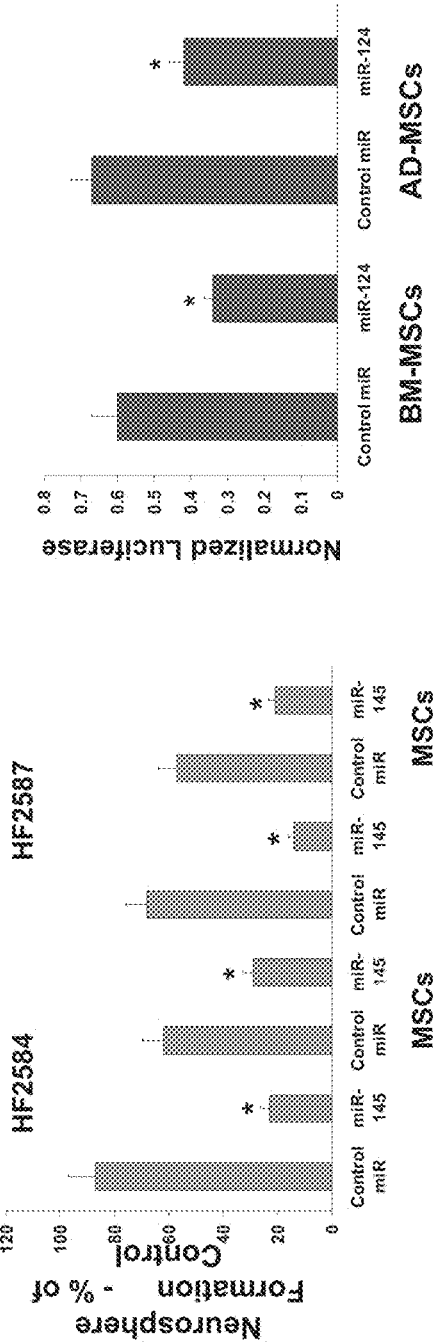

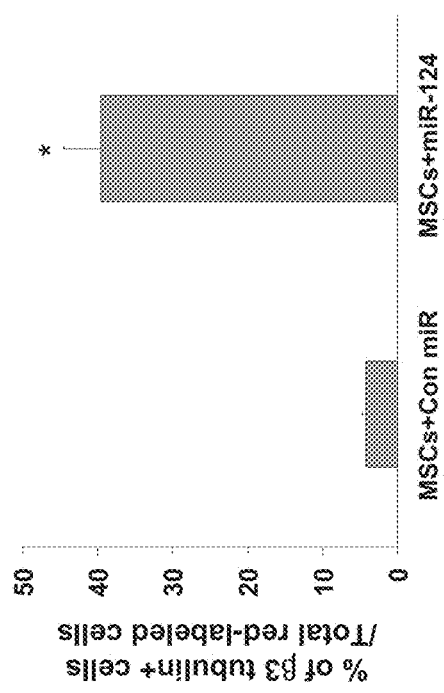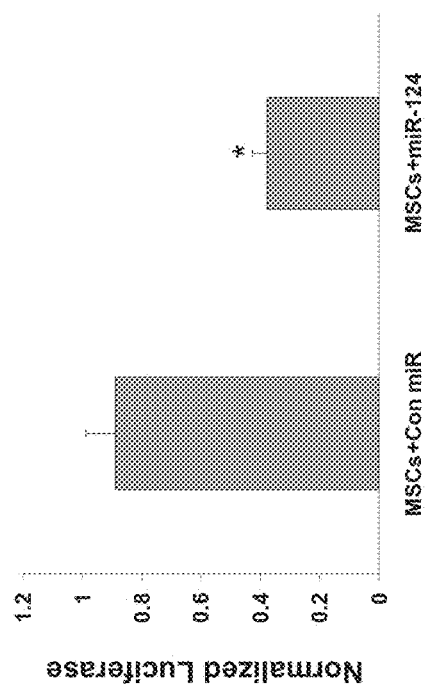

METHODS OF GENERATING OLIGODENDROCYTES AND CELL POPULATIONS COMPRISING SAME

RELATED APPLICATIONS

This application is a National Phase of PCT Patent Application No. PCT/IL2011/000660 having International filing date of Aug. 14, 2011, which claims the benefit of priority under 35 USC §119(e) of U.S. Provisional Patent Applications Nos. 61/373,909 filed on Aug. 16, 2010 and 61/433,301 filed on Jan. 17, 2011. The contents of the above applications are all incorporated by reference as if fully set forth herein in their entirety.

SEQUENCE LISTING STATEMENT

The ASCII file, entitled 55933SequenceListing.txt, created on Feb. 12, 2013, comprising 29,593 bytes, submitted concurrently with the filing of this application is incorporated herein by reference.

FIELD AND BACKGROUND OF THE INVENTION

The present invention, in some embodiments thereof, relates to methods of generating oligodendrocytes or oligodendrocytes progenitors from mesenchymal stem cells and cell populations comprising same.

Oligodendrocytes are important cells in the CNS that synthesize multilamellar myelin membranes that ensheath axons and therefore play an important role in the development and function of the CNS. Demyelination disrupts nerve conduction and leads to nerve degeneration which is associated with various disorders including Multiple Sclerosis (MS).

Oligodendrocytes are derived from multipotent neural progenitor cells. Various transcription factors and signaling pathways have been associated with this process, including Olig1, NKX2.2, SHH, Wnt and Notch (2).

For example, early oligodendrogenesis is regulated by the basic helix-loop-helix transcription factors Olig1 and Olig2. The expression of these transcription factors persists as oligodendrocyte progenitors leave the ventricular zone and become mature oligodendrocytes. During the time when oligodendrocytes migrate into the white matter, they acquire the expression of two additional transcription factors, Sox10 and Nkx2.2. The expression of these two transcription factors directly regulates the expression of the myelin gene and the differentiation of oligodendrocytes.

Multiple Sclerosis is a disease caused by chronic autoimmune inflammatory process resulting in patches of demyelination that affects the central nervous system (11). Remyelination, a regenerative process in which axons in the CNS are reinvested with new myelin sheaths and pre-lesion architecture and functions are restored, is mainly mediated by a population of cell specific adult stem/progenitor cells that are called oligodendrocyte precursor/progenitor cells (OPC) or glial precursor/progenitor cells. These cells are distributed in the white and grey matter throughout adulthood. Failure of remyelination predisposes axons to degeneration, a reversible process which is associated with the progressive deterioration of the disease. Therefore, remyelination is considered an important clinical objective in MS in order to slow or prevent axonal degradation and to preserve long-term axonal survival in the brain and spinal cord.

Mesenchymal stem cells (MSCs) are a heterogeneous population of stromal cells isolated from multiple species, residing in most connective tissues including bone marrow, adipose, umbilical cord, placenta, amniotic fluid and perivascular tissues. MSC can differentiate into cells of the mesenchymal lineage, such as bone, cartilage and fat but, under certain circumstances, have been reported to acquire the phenotype of cells of the endodermal and neuroectodermal lineage, suggesting some potential for "transdifferentiation". Within the bone marrow these cells are tightly intermingled with and support hematopoiesis and the survival of hematopoietic stem cells in acquiescent state (7). In addition, MSCs derived from the bone marrow, adipose tissue or the cord/placenta have unique properties after expansion in culture including their ability to modulate innate and adaptive immunity (8). Furthermore, MSCs migrate to sites of inflammation and protect damaged tissues, including the CNS, properties that supported their use as new immunosuppressive or rather immunoregulatory or anti-inflammatory agents for the treatment of inflammatory and immune-mediated diseases including autoimmune disorders (9).

Recent reports have demonstrated that MSCs also have the potential to differentiate into functional neuronal cells. MSCs have been shown to exert therapeutic effects in a variety of neurological diseases and dysfunctions in experimental animal models and more recently in pilot clinical trials. Their effects have been mainly attributed to immunosuppressive and neuroprotective functions. However, some studies demonstrated that neural differentiation of these cells increased their therapeutic effect in various instances. Therefore, the use of MSC-derived neuronal cells has a great potential as an easily accessible source of autologous cells for treatment of inflammatory and neurodegenerative disorders including Multiple Sclerosis, ALS and Parkinson's disease aiming for both cell mediated control of disease activity as well as regeneration of damaged or lost functions.

In experimental autoimmune encephalitis (EAE), an animal model of MS, treatment of mice with bone marrow derived MSCs resulted in significant suppression of disease manifestations in parallel with down-regulation of cell-mediated anti-self reactivity (9). The migration of bone marrow derived MSCs paralleled improvement of the clinical outcome of treated recipients (9). Using genetically transduced green fluorescent donors in these animal models, donor derived cells migrating into the brain acquired phenotypic markers of neurons, astrocytes and oligodendrocytes in parallel with improvement of clinical signs of disease as was also confirmed by histopathological evaluation of treated as compared with untreated controls. Interestingly, transplantation of glial committed progenitor into a viral model of MS resulted in some degree of remyelination (12), suggesting that the strategy of transplantation of oligodendrocytic progenitors is worthwhile pursuing.

Studies using injection of enriched and unmodified autologous bone marrow derived and more recently also adipose tissue derived MSC which can be prepared from liposuction intrathecally and intravenously suggests that some patients with otherwise resistant MS may benefit from treatment with autologous MSCs; however, complete restoration of all neurological deficits in patients with advanced and long-lasting disease has not yet been achieved (13). Iron nanoparticle (Feridex™) labeled MSCs injected intrathecally and intravenously could be documented in the brain by MRI, thus confirming that these cells can actively migrate into the central nervous system.

Liu et al [Dev Biol. 302:683-693, 2007] have reported oligodendrocytic differentiation of bone marrow derived mesenchymal cells. This study employed fetal cells and used transfection with the transcription factors Olig2 and NKX.2.

U.S. Patent Application No. 20100021434 teaches oligodendrocytic differentiation of bone marrow derived mesenchymal cells by incubation in N2 supplement and fibroblast growth factor (FGF).

International Patent Application WO2010111522 teaches mesenchymal stem cells which secrete and deliver microRNAs for the treatment of diseases.

International Patent Application WO2010144698 teaches expression of miRNAs in mesenchymal stem cells to induce neuronal differentiation thereof.

SUMMARY OF THE INVENTION

According to an aspect of some embodiments of the present invention there is provided a method of generating a population of cells useful for treating a nerve disease or disorder in a subject, the method comprising contacting mesenchymal stem cells (MSCs) with at least one exogenous miRNA selected from the group consisting of miR-145, miR-30d, miR-125b, miR-128, miR-181c, miR-26a, miR-196, miR-10b, miR-25, miR-424, miR19 and miR149, thereby generating the population of cells.

According to an aspect of some embodiments of the present invention there is provided a method of generating a population of cells useful for treating a nerve disease or disorder in a subject, the method comprising expressing in mesenchymal stem cells (MSCs) exogenous NKX2.2 and/or Olig2, thereby generating the population of cells.

According to an aspect of some embodiments of the present invention there is provided a method of generating a population of cells useful for treating a central nervous system (CNS) disorder in a subject, the method comprising contacting mesenchymal stem cells (MSCs) with an agent that downregulates an amount and/or activity of connective tissue growth factor (CTGF), thereby generating the population of cells.

According to an aspect of some embodiments of the present invention there is provided an isolated population of cells generated according to the method of the present invention having an oligodendrocyte phenotype.

According to an aspect of some embodiments of the present invention there is provided a method of treating a nerve disease or disorder in a subject in need thereof, the method comprising administering to the subject a therapeutically effective amount of the isolated population of cells of the present invention, thereby treating the brain disease or disorder.

According to an aspect of some embodiments of the present invention there is provided a pharmaceutical composition comprising the isolated population of cells of the present invention and a pharmaceutically acceptable carrier.

According to an aspect of some embodiments of the present invention there is provided a cell culture comprising mesenchymal stem cells which comprise at least one miRNA selected from the group consisting of miR-128, miR-9, miR-9*, miR124, miR137 and miR218 and a culture medium, said culture medium not being a differentiating medium.

According to an aspect of some embodiments of the present invention there is provided a method of treating a nerve disease or disorder in a subject in need thereof, the method comprising:

(a) contacting a population of mesenchymal stem cells with at least one therapeutic miRNA, wherein said contacting is effected for less than 5 days; and (b) transplanting a therapeutically effective amount of said mesenchymal stem cells which have been modified to comprise said therapeutic miRNA to the brain of the subject, said miRNA being selected from the group consisting of miR-128, miR-9, miR-9*, miR124, miR137 and miR218, thereby treating the nerve disease or disorder.

According to an aspect of some embodiments of the present invention there is provided a method of treating a brain tumor in a subject in need thereof, the method comprising transplanting a therapeutically effective amount of mesenchymal stem cells which have been modified to express at least one exogenous miRNA selected from the group consisting of miR-9, miR-124, miR-137, miR-218 and miR-212, thereby treating the brain tumor.

According to some embodiments of the invention, the at least sequence is selected from the group consisting of miR-145, miR-30d, miR-125b, miR-128, miR-181c.

According to some embodiments of the invention, the MSCs are isolated from a tissue selected from the group consisting of bone marrow, adipose tissue, placenta, cord blood and umbilical cord.

According to some embodiments of the invention, the MSCs are autologous to said subject.

According to some embodiments of the invention, the MSCs are non-autologous to said subject.

According to some embodiments of the invention, the MSCs are semi-autologous to said subject.

According to some embodiments of the invention, the contacting is effected by transfecting said MSCs with said at least one miRNA.

According to some embodiments of the invention, the contacting is effected by transfecting said MSCs with an expression vector which comprises a polynucleotide sequence which encodes a pre-miRNA of said at least one miRNA.

According to some embodiments of the invention, the contacting is effected by transfecting said MSCs with an expression vector which comprises a polynucleotide sequence which encodes said at least one miRNA.

According to some embodiments of the invention, at least 50% of the population of cells express at least one marker selected from the group consisting of GalC, O4, O1, CNPase, MOG and MBP.

According to some embodiments of the invention, the MSCs are incubated in a medium comprising at least one agent selected from the group consisting of insulin, hydrocortisone, transferrin, pyruvate, ciliary neurotrophic factor (CNTF), neurotrophin 3 (NT-3), heregulin, erythropoietin, PDGF-AA and tri-iodothyronine following, prior to or concomitant with said contacting.

According to some embodiments of the invention, the method further comprises expressing in said MSCs an exogenous differentiation factor selected from the group consisting of CNTF, NT-3, erythropoietin, NKX2.2 and Olig2 following, prior to or concomitant with said contacting.

According to some embodiments of the invention, the MSCs are isolated from a tissue selected from the group consisting of bone marrow, adipose tissue, placenta, cord blood and umbilical cord.

According to some embodiments of the invention, the MSCs are autologous to said subject.

According to some embodiments of the invention, the MSCs are non-autologous to said subject.

According to some embodiments of the invention, the MSCs are semi-autologous to said subject.

According to some embodiments of the invention, the agent is a polynucleotide agent.

According to some embodiments of the invention, the agent is an antibody.

According to some embodiments of the invention, the polynucleotide agent comprises an siRNA agent.

According to some embodiments of the invention, the MSCs are incubated in a medium comprising at least one agent selected from the group consisting of insulin, hydrocortisone, transferrin, pyruvate, ciliary neurotrophic factor (CNTF), neurotrophin 3 (NT-3), heregulin, erythropoietin, PDGF-AA and tri-iodothyronine following, prior to or concomitant with said contacting.

According to some embodiments of the invention, the isolated population of cells are genetically modified.

According to some embodiments of the invention, the isolated population of cells comprises an exogenous miRNA selected from the group consisting of miR-145, miR-30d, miR-125b, miR-128, miR-181c, miR-26a, miR-196, miR-10b, miR-25, miR-424, miR19 and miR149.

According to some embodiments of the invention, the isolated population of cells are for use in treating a brain disease or disorder.

According to some embodiments of the invention, the brain disease or disorder is a neurodegenerative disorder.

According to some embodiments of the invention, the neurodegenerative disorder is selected from the group consisting of multiple sclerosis, Parkinson's, epilepsy, amyotrophic lateral sclerosis (ALS), stroke, autoimmune encephalomyelitis, diabetic neuropathy, glaucomatous neuropathy, Alzheimer's disease and Huntingdon's disease.

According to some embodiments of the invention, the brain disease of disorder is multiple sclerosis.

According to some embodiments of the invention, the nerve disease or disorder is a neurodegenerative disorder.

According to some embodiments of the invention, the neurodegenerative disorder is selected from the group consisting of multiple sclerosis, Parkinson's, epilepsy, amyotrophic lateral sclerosis (ALS), stroke, autoimmune encephalomyelitis, diabetic neuropathy, glaucomatous neuropathy, Alzheimer's disease and Huntingdon's disease.

According to some embodiments of the invention, the neurodegenerative disease is multiple sclerosis.

According to some embodiments of the invention, the nerve disease or disorder comprises a spinal cord injury.

According to some embodiments of the invention, the mesenchymal stem cells have been genetically modified to express said at least one therapeutic miRNA.

According to some embodiments of the invention, the nerve disease or disorder is a brain tumor.

According to some embodiments of the invention, the brain tumor is a glioma.

According to some embodiments of the invention, the method further comprises expressing in the mesenchymal stem cells a pro-apoptotic agent.

According to some embodiments of the invention, the pro-apoptotic agent comprises soluble TNF-related apoptosis-inducing ligand (sTRAIL).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a diagram of an exemplary vector used to transfect mesenchymal stromal stem cells in order to analyze its differentiation status.

Figures 2A, 2B:
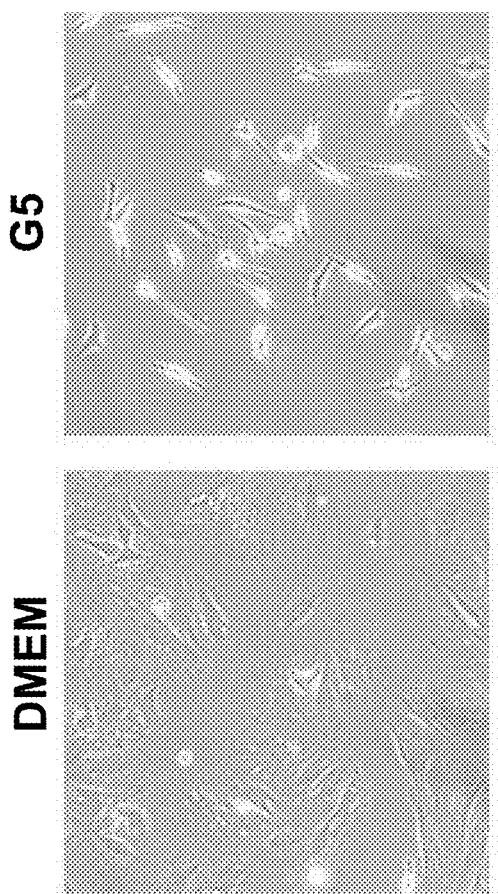

FIGS. 2A-B illustrate that incubation of BM-derived MSCs in G5 medium induces changes in the morphology of the cells to OPC characteristics.

FIG. 3 illustrates that incubation of BM-derived MSCs in G5 medium induces the expression of the OPC markers, Olig2 and NKX2.2.

FIGS. 4A-F are photographs illustrating differentiation of MSCs transfected with miR-145 for 12 days in G5 medium. Cells were transfected with miR-145 and maintained in G5 medium. Cells were stained with anti-MOG antibody. The results are representative of five similar experiments.

FIGS. 5A-D are photographs illustrating that miR-145 induces the expression of GalC in BM-MSCs. Cells were transfected with miR-145 and maintained in G5 medium. Cells were stained with anti-GalC antibody. The results are representative of five similar experiments.

FIG. 6 illustrates that miR-145 induces the expression of CNPase in BM-MSCs. Cells were transfected with miR-145 mimic and were then maintained in NM or G5 medium for 12 days. The expression of CNPase was determined using Western blot analysis. Actin expression was determined to demonstrate equal protein loading. The results are representative of five similar experiments.

FIGS. 7A-F are photographs illustrating induction of O4 in BM-MSCs by miR-145. Cells were transfected with miR-145 and maintained in G5 medium. Cells were stained with anti-O4 antibody. The results are representative of five similar experiments.

Figure 8:
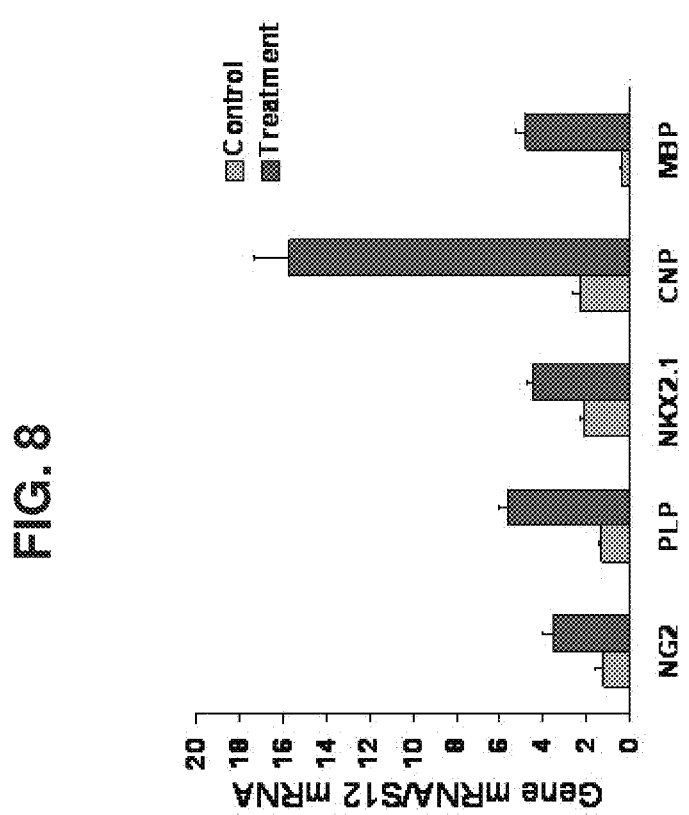

FIG. 8 is a graph illustrating expression of oligodendrocyte markers in MSCs transfected with miR-145. The expression of various oligodendrocytic markers was examined 12 days following transfection using qRT-PCR. The results are representative of four similar experiments. NG2-proteoglycan (developing and adult oligodendrocyte precursor cells); PLP—myelin protelipid protein; NKX2.1—transcription factor, oligodendrocyte progenitors; CNP—development and differentiation of oligodendrocytes; MBP—myelin basic protein, oligodendrocytes.

FIGS. 9A-B are photographs illustrating induction of MBP in BM-MSCs. Cells were transfected with miR-145 and maintained in medium supplemented with oligodendrocytic promoting medium for 12 days. The induction of the oligodendrocyte reporter, MBP-GFP was analyzed using a fluorescent microscope. The results are representative of five similar experiments.

FIGS. 10A-B are graphs illustrating that miR-145 induces the expression of MBP-GFP in MSCs. BM-derived MSCs were transfected with MBP-GFP and with miR-145 for 12 days in G5 medium. The fluorescence of the MBP-GFP was determined using FACS analysis. The results represent three different experiments.

Figure 11:
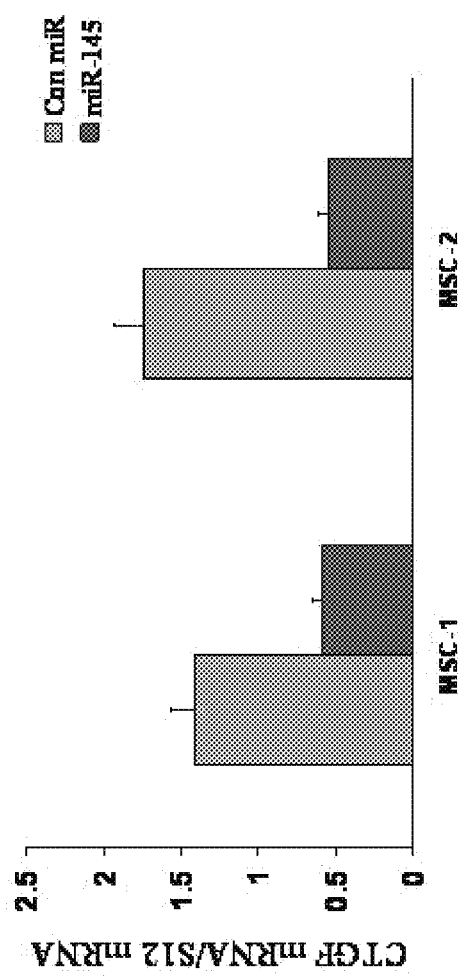

FIG. 11 is a graph illustrating that miR-145 decreases the expression of CTGF. Two different preparations of BM-MSCs were transfected with miR-145. mRNA was extracted after 3 days and the expression of CTGF was then examined using real-time PCR. The results represent the means±SD of three separate experiments.

Figure 12:
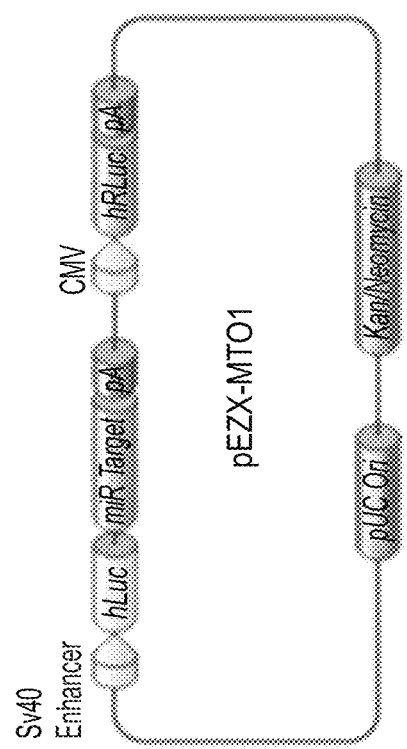

FIG. 12 is a graphical illustration of an expression construct used to determine whether miR-145 binds to the 3' UTR of CTGF.

Figure 13:
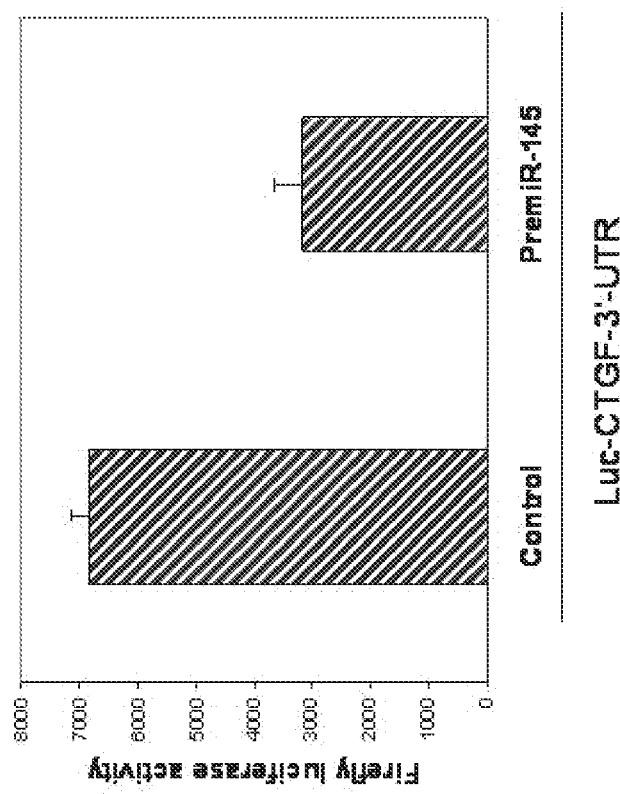

FIG. 13 is a graph illustrating target validation of miR-145. 3'-UTR-CTGF and a scrambled control were cloned into a luciferase reporter plasmid (FIG. 12) and co-transfected with miR-145 mimic into MSCs. The luciferase activity of these cells was measured 72 hours thereafter. As presented in FIG. 12, miR-145 significantly decreased the luciferase activity of the 3'-UTR-CTGF, whereas it did not affect that of the CV. Likewise, a control miR did not alter the luciferase activity of cells co-transfected with the 3'-UTR-CTGF. The results represent the means±SD of three separate experiments.

Figure 14:
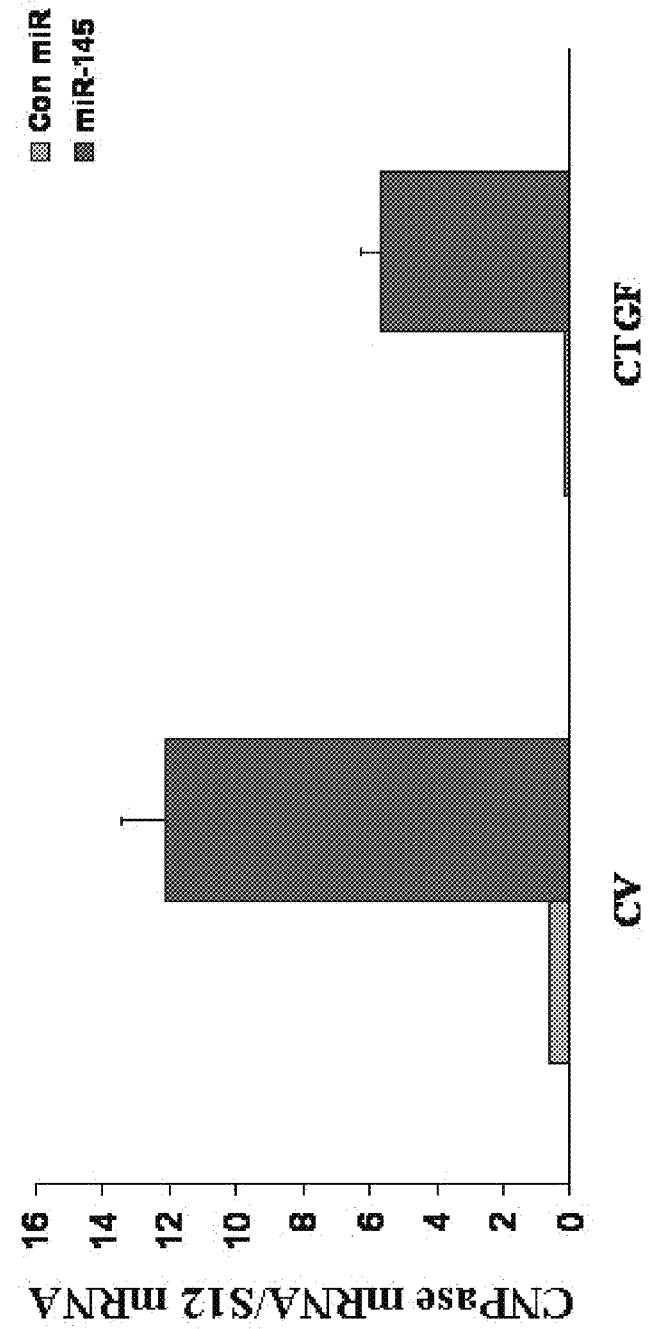

FIG. 14 is a graph illustrating that the decrease in CTGF expression plays a role in the oligodendrocytic differentiation induced by miR-145. MSCs were transfected with a CTGF construct that lacks the 3' UTR followed by transfection with a miR-145 mimic. The expression of CNPase mRNA was examined 12 days later using real-time PCR. The results are representative of five similar experiments.

FIGS. 15A-B illustrates bone marrow (BM)-MSCs transfer miRs to co-cultured glioma cells. BM-derived MSCs were transfected with a control miR or with a miR-124 mimic labeled with FAM (A). BM-MSCs and AD-MSCs were transfected with miR-145-FITC (B). Following 24 hr, U87 cells (A) or A172 cells (B) labeled with CellTracker Red were added to the MSC culture and the expression of the fluorescent miR-124 or miR-145 was analyzed 24 hours later using a confocal microscope. The results are representative of three different experiments that gave similar results.

Figure 16:
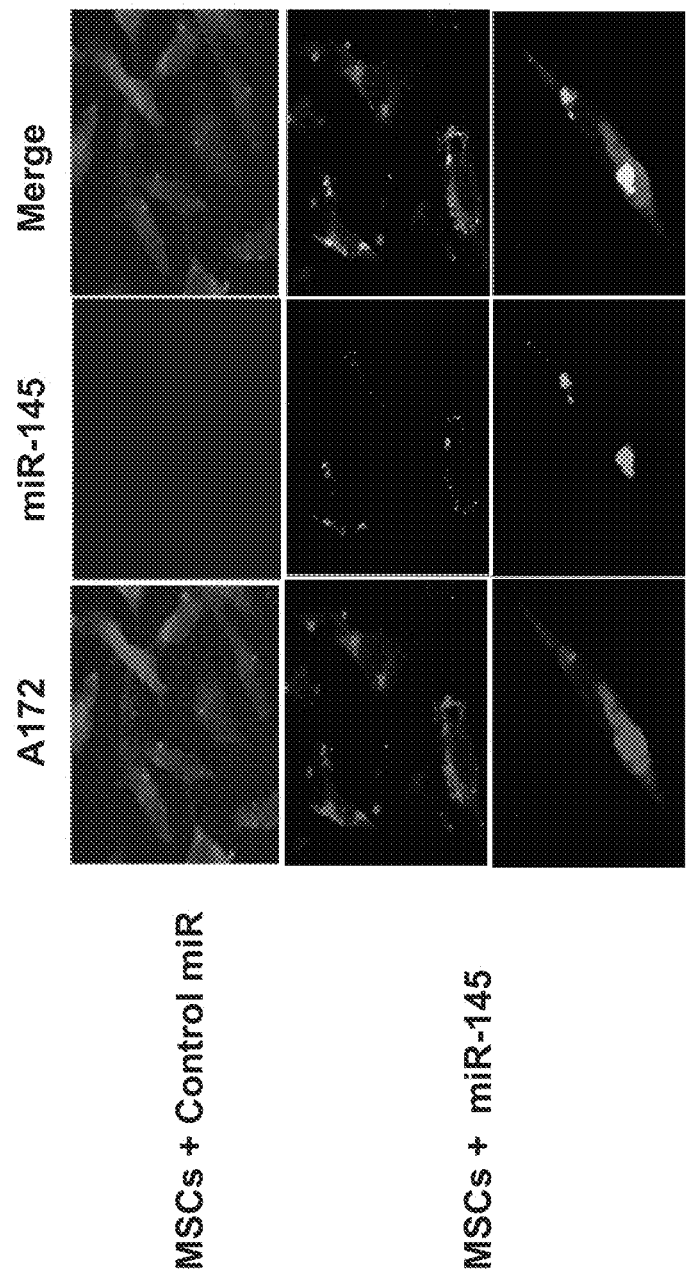

FIG. 16 illustrates in situ hybridization of miR-145 in gliomas cells. BM-MSCs were transfected with a miR-145 mimic and were co-cultured with U87 cells labeled with CellTracker Red for additional 24 hr. In situ hybridization of miR-145 was then performed and the red labeled cells were visualized for the presence of green labeled miR-145.

FIGS. 17A-B are graphs illustrating that transferred miR-124 downregulates the expression of SCP-1 in glioma cells. U87 cells were transfected with a miR-124 mimic and the expression of SCP_1 was examined using qRT-PCR after 3 days (A). U87 cells were transfected with a construct expressing SCP-1 3'-UTR conjugated to luciferase. The cells were then co-cultured with BM-MSCs or AD-MSCs that were transfected with either a control miRNA or miR-124 mimic for 24 hr. The luciferase activity of the cells was determined after 72 hr of co-culture (B). The results the mean±SE of three different experiments. *p<0.001.

FIGS. 18A-D illustrate that transferred miR-124 decreases the migration of glioma cells. U87 cells were transfected with a miR-124 mimic and cell migration was determined 48 hr later using transwell migration (A). U87 cells (A,B) or cells labeled with CellTracker Red (C,D) were cultured with BM-MSCs expressing either a control miRNA or miR-124 mimic. The migration of the U87 cells (A,B) or the red labeled U87 cells (C.D) was determined after 48 hr using transwell migration assay. The results are representative of three different experiments that gave similar results. *p<0.001.

FIGS. 19A-C illustrate that MSCs transfer miR mimics to glioma stem cells (GSCs) and decrease their self-renewal. BM-MSCs or AD-MSCs were transfected with fluorescent miR-124 or miR-145 or with miR 124 and 145 mimics After 24 hr, HF 2584 GSCs labeled with CellTracker Red were added to the cultured MSCs for additional 24 hr. The expression of the fluorescent miRs was analyzed using a confocal microscope (A). HF-2584 or HF2587 GSCs co-cultured with BM-MSCs or AD-MSCs transfected with either a control miR or miR-145 mimic were collected after 24 hr of co-culture and were analyzed for self renewal for 10 days (B). BM-MSC and AD-MSCs were transfected with a control miR or with a miR-124 mimic. After 24 hr, HF2587 GSCs transfected with a plasmid of 3'-UTR SCP-1 tagged to luciferase were added to the cultured MSCs. The luciferase activity of SCP-1-3'UTR expressed in the GSCs was analyzed after 48 hour (C). The results are representative of three different experiments that gave similar results. *p<0.001.

FIGS. 20A-B illustrate that MSCs transfer neuronal miR mimics to neural progenitor cells and promote their neuronal differentiation. BM-MSCs or AD-MSCs (data not shown) were transfected with a miR 124 mimics or a control miR. After 24 hr, the RenCell neural progenitor cells labeled with CellTracker Red were added to the cultured MSCs for additional 24 hr. The percentage of β3-tubulin+ cells out of the CellTracker Red-labeled cells were determined for both REN cells co-cultured with MSCs transfected with a control miR or with MSCs transfected with miR-124 using a fluorescent microscope (A). BM-MSC and AD-MSCs (data not shown) were transfected with a control miR or with a miR-124 mimic. After 24 hr, REN cells transfected with a plasmid of 3'-UTR SCP-1 tagged to luciferase were added to the cultured MSCs. The luciferase activity of SCP-1-3'UTR expressed in the REN cells was analyzed after 48 hr (C). The results are representative of three different experiments that gave similar results. *p<0.001.

Figure 21:
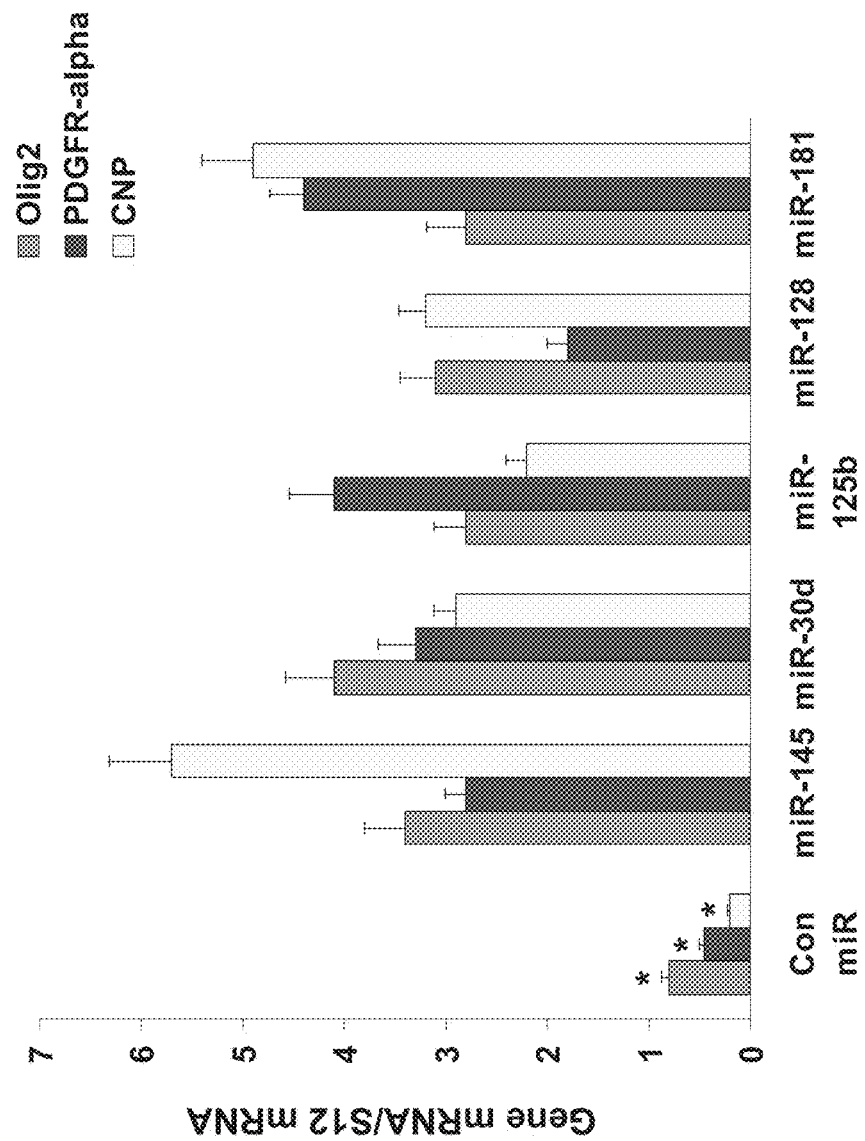

FIG. 21 is a bar graph illustrating the expression of oligodendrocyte markers in MSCs transfected with miR-145, miR-30d, miR-125b, miR-128 and miR-181 maintained in G5 medium.

Figure 22:
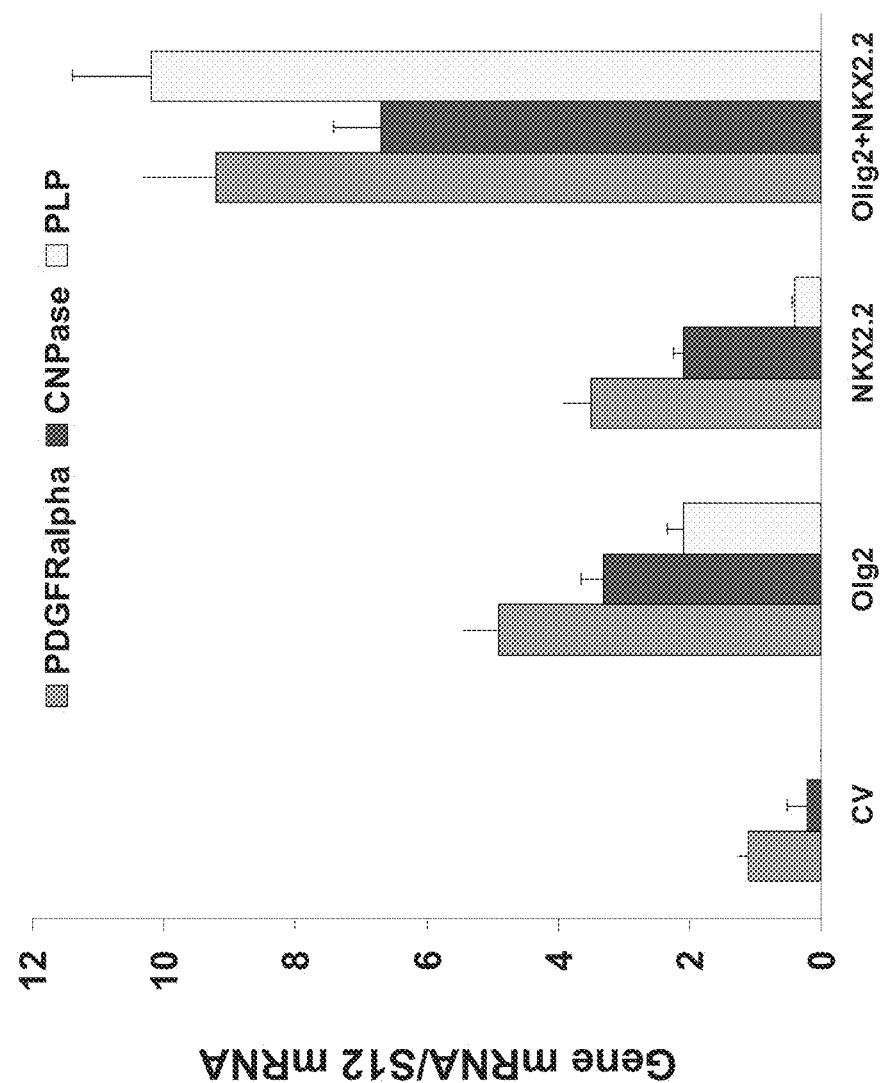

FIG. 22 is a bar graph illustrating the expression of oligodendrocyte markers in MSCs genetically modified to express NKX2.2 and/or Olig2.

DESCRIPTION OF SPECIFIC EMBODIMENTS OF THE INVENTION

The present invention, in some embodiments thereof, relates to methods of generating oligodendrocytes from mesenchymal stem cells and cell populations comprising same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways including the use of MSCs as carriers for delivery of miRs into adjacent normal or malignant target cells.

The importance of myelination is demonstrated by the demyelinating disease multiple sclerosis, in which myelin sheaths in some regions of the central nervous system are destroyed by an unknown mechanism. The significance of myelination is also demonstrated in many other neurodegenerative diseases, in which myelinated neurons are injured. Where this happens, the propagation of nerve impulses is greatly slowed, often with devastating neurological consequences.

Restoration of myelin has been proposed as a treatment therapy in order to address the underlying cause of such diseases. However, obtaining large numbers of myelinating cells for transplantation remains a major stumbling block.

Whilst reducing the present invention to practice, the present inventors have found that a number of micro RNAs (miRNAs) including miR-145, miR-125b, miR128 and miR-30d induce oligodendrocytic differentiation of bone marrow, adipose-derived, amniotic fluid and cord/placenta derived mesenchymal stem cells (MSCs) and propose that such differentiated MSCs may be used to treat patients with brain diseases or disorders.

Specifically, the present inventors have shown that transfection of MSCs with the miRNAs listed above change the morphological appearance of the cells and further increase expression of various oligodendrocytic markers therein, as assessed by RT-PCR, Western Blot and immunohistochemistry (FIGS. 4A-F, 5A-D, 6 7A-F, 8, and 9A-B).

The present inventors further identified CTGF as a novel target of miR-145 and as an important mediator of the effect of this miRNA on the oligodendrocytic differentiation of miR-145. Therefore, the present inventors propose blocking anti-CTGF antibodies or silencing of CTGF in order to differentiate MSCs towards an oligodendrocytic phenotype.

Thus, according to one aspect of the present invention there is provided a method of generating a population of cells useful for treating a nerve disease or disorder in a subject, the method comprising contacting (either ex vivo or in vivo) mesenchymal stem cells (MSCs) with at least one miRNA selected from the group consisting of miR-145, miR-30d, miR-125b, miR-128, miR-181c, miR-26a, miR-196, miR-10b, miR-25, miR-424, miR19 and miR149, thereby generating the population of cells.

Mesenchymal stem cells give rise to one or more mesenchymal tissues (e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines. Although such cells can be isolated from embryonic yolk sac, placenta, umbilical cord, fetal and adolescent skin, blood and other tissues, their abundance in the easily accessible fat tissue and BM far exceeds their abundance in other tissues and as such isolation from BM and fat tissue is presently preferred.

Methods of isolating, purifying and expanding mesenchymal stem cells (MSCs) are known in the arts and include, for example, those disclosed by Caplan and Haynesworth in U.S. Pat. No. 5,486,359 and Jones E. A. et al., 2002, Isolation and characterization of bone marrow multipotential mesenchymal progenitor cells, Arthritis Rheum. 46(12): 3349-60.

Mesenchymal stem cells may be isolated from various tissues including but not limited to bone marrow, peripheral blood, blood, placenta (e.g. fetal side of the placenta), cord blood, umbilical cord, amniotic fluid, placenta and from adipose tissue.

A method of isolating mesenchymal stem cells from peripheral blood is described by Kassis et al [Bone Marrow Transplant. 2006 May; 37(10):967-76]. A method of isolating mesenchymal stem cells from placental tissue is described by Zhang et al [Chinese Medical Journal, 2004, 117 (6):882-887]. Methods of isolating and culturing adipose tissue, placental and cord blood mesenchymal stem cells are described by Kern et al [Stem Cells, 2006; 24:1294-1301]1.

According to a preferred embodiment of this aspect of the present invention, the mesenchymal stem cells are human.

According to another embodiment of this aspect of the present invention, the mesenchymal stem cells are isolated from newborn humans.

Bone marrow can be isolated from the iliac crest of an individual by aspiration. Low-density BM mononuclear cells (BMMNC) may be separated by a FICOL-PAQUE density gradient or by elimination of red blood cells using Hetastarch (hydroxyethyl starch). Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, a medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 μg/ml streptomycin (GIBCO); and 2 mM L-glutamine (GIBCO). Resuspended cells are plated in about 25 ml of medium in a 10 cm culture dish (Corning Glass Works, Corning, N.Y.) and incubated at 37° C. with 5% humidified $CO_2$. Following 24 hours in culture, nonadherent cells are discarded, and the adherent cells are thoroughly washed twice with phosphate buffered saline (PBS). The medium is replaced with a fresh complete medium every 3 or 4 days for about 14 days. Adherent cells are then harvested with 0.25% trypsin and 1 mM EDTA (Trypsin/EDTA, GIBCO) for 5 min at 37° C., replated in a 6-cm plate and cultured for another 14 days. Cells are then trypsinized and counted using a cell counting device such as for example, a hemocytometer (Hausser Scientific, Horsham, Pa.). Cultured cells are recovered by centrifugation and resuspended with 5% DMSO and 30% FCS at a concentration of 1 to $2\times10^6$ cells per ml. Aliquots of about 1 ml each are slowly frozen and stored in liquid nitrogen.

Adipose tissue-derived MSCs can be obtained by liposuction and mononuclear cells can be isolated manually by removal of the fat and fat cells, or using the Celution System (Cytori Therapeutics) following the same procedure as described above for preparation of MSCs.

According to one embodiment the populations are plated on polystyrene plastic surfaces (e.g. in a flask) and mesenchymal stem cells are isolated by removing nonadherent cells. Alternatively mesenchymal stem cell may be isolated by FACS using mesenchymal stem cell markers.

Preferably the MSCs are at least 50% purified, more preferably at least 75% purified and even more preferably at least 90% purified.

To expand the mesenchymal stem cell fraction, frozen cells are thawed at 37° C., diluted with a complete medium and recovered by centrifugation to remove the DMSO. Cells are resuspended in a complete medium and plated at a concentration of about 5,000 cells/cm². Following 24 hours in culture, nonadherent cells are removed and the adherent cells are harvested using Trypsin/EDTA, dissociated by passage through a narrowed Pasteur pipette, and preferably replated at a density of about 1.5 to about 3.0 cells/cm². Under these conditions, MSC cultures can grow for about 50 population doublings and be expanded for about 2000 fold [Colter D C., et al. Rapid expansion of recycling stem cells in cultures of plastic-adherent cells from human bone marrow. Proc Natl Acad Sci USA. 97: 3213-3218, 2000].

MSC cultures utilized by some embodiments of the invention preferably include three groups of cells which are defined by their morphological features: small and agranular cells (referred to as RS-1, herein below), small and granular cells (referred to as RS-2, hereinbelow) and large and moderately granular cells (referred to as mature MSCs, hereinbelow). The presence and concentration of such cells in culture can be assayed by identifying a presence or absence of various cell surface markers, by using, for example, immunofluorescence, in situ hybridization, and activity assays.

When MSCs are cultured under the culturing conditions of some embodiments of the invention they exhibit negative staining for the hematopoietic stem cell markers CD34, CD11B, CD43 and CD45. A small fraction of cells (less than 10%) are dimly positive for CD31 and/or CD38 markers. In addition, mature MSCs are dimly positive for the hematopoietic stem cell marker, CD117 (c-Kit), moderately positive for the osteogenic MSCs marker, Stro-1 [Simmons, P. J. & Torok-Storb, B. (1991). Blood 78, 5562] and positive for the thymocytes and peripheral T lymphocytes marker, CD90 (Thy-1). On the other hand, the RS-1 cells are negative for the CD117 and Stro1 markers and are dimly positive for the CD90 marker, and the RS-2 cells are negative for all of these markers.

The mesenchymal stem cells of the present invention may be of a syngeneic or allogeneic source, as further described herein below.

Differentiation of the mesenchymal stem cells can be induced by incubating the MSCs in differentiating media such as those described in U.S. Pat. No. 6,528,245 and by Sanchez-Ramos et al. (2000); Woodburry et al. (2000); Woodburry et al. (J. Neurisci. Res. 96:908-917, 2001); Black and Woodbury (Blood Cells Mol. Dis. 27:632-635, 2001); Deng et al. (2001), Kohyama et al. (2001), Reyes and Verfatile (Ann. N.Y. Acad. Sci. 938:231-235, 2001) and Jiang et al. (Nature 418:47-49, 2002).

The differentiating media may be DMEM or DMEM/F12, OptiMEM™ or any other medium that supports neuronal growth. According to a preferred embodiment of this aspect of the present invention, the medium comprises neurobasal medium (e.g. Cat. No. 21103049, Invitrogen, Calif., U.S.A.).

According to another embodiment of this aspect of the present invention, the medium is supplemented with at least one of insulin, hydrocortisone, transferring, pyruvate and nicotinamide. According to another embodiment, the medium comprises G5™ supplement (Catalogue No. F001-003, PAA Laboratories).

As mentioned, the mesenchymal stem cells are contacted (either ex vivo or in vivo) with at least one of the following miRNAs in order to induce differentiation into oligodendrocyte-like cells—miR-145 (SEQ ID NO: 15), miR-30d (SEQ ID NO: 16), miR-125b (SEQ ID NO: 17), miR-128 (SEQ ID NO: 18), miR-181c (SEQ ID NO: 19), miR-26a (SEQ ID NO: 27), miR-196 (SEQ ID NO: 28), miR-10b (SEQ ID NO: 31), miR-25 (SEQ ID NO: 32), miR-424 (SEQ ID NO: 33), miR19 (SEQ ID NO: 34) and miR149 (SEQ ID NO: 35).

It will be appreciated that prior to contacting with one of the above mentioned miRNAs, the MSCs may be contacted with additional miRNAs that serve to induce dedifferentiation of the cells into pluripotent cells. Such miRNAs include transfecting with a microRNA-302bcad/367 (SEQ ID NOs: 42, 44, 36, 48 and 50).

The term "microRNA", "miRNA", and "miR" are synonymous and refer to a collection of non-coding single-stranded RNA molecules of about 19-28 nucleotides in length, which regulate gene expression. miRNAs are found in a wide range of organisms and have been shown to play a role in development, homeostasis, and disease etiology.

Below is a brief description of the mechanism of miRNA activity.

Genes coding for miRNAs are transcribed leading to production of an miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nt precursor known as the pre-miRNA. Drosha cleaves the pri-miRNA with a staggered cut typical of RNase III endonucleases yielding a pre-miRNA stem loop with a 5' phosphate and ~2 nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor exportin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

MiRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise any of the sequences of SEQ ID NOS: 15-19 or 27-39, or variants thereof.

It will be appreciated from the description provided herein above, that contacting mesenchymal stem cells may be affected in a number of ways:

1. Transiently transfecting the mesenchymal stem cells with the mature double stranded miRNA;
2. Stably, or transiently transfecting the mesenchymal stem cells with an expression vector which encodes the mature miRNA (SEQ ID NOs: 15-19 or 27-39).
3. Stably, or transiently transfecting the mesenchymal stem cells with an expression vector which encodes the pre-miRNA (SEQ ID NOs: 20-24 and 52-71). The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of the miRNA—i.e. SEQ ID NOs: 15-19 or 27-39 or variants thereof.
4. Stably, or transiently transfecting the mesenchymal stem cells with an expression vector which encodes the pri-miRNA. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. Preparation of miRNAs mimics can be effected by chemical synthesis methods or by recombinant methods.

To express miRNAs in mesencyhymal stem cells, a polynucleotide sequence encoding the miRNA (or pre-miRNA, or pri-miRNA) is preferably ligated into a nucleic acid construct suitable for mesenchymal stem cell expression. Such a nucleic acid construct includes a promoter sequence for directing transcription of the polynucleotide sequence in the cell in a constitutive or inducible manner.

It will be appreciated that the nucleic acid construct of some embodiments of the invention can also utilize miRNA homologues which exhibit the desired activity (i.e., oligodendrocytic differentiating ability). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any of the sequences SEQ ID NOs:15-19 or 27-39, as determined using the BestFit software of the Wisconsin sequence analysis package, utilizing the Smith and Waterman algorithm, where gap weight equals 50, length weight equals 3, average match equals 10 and average mismatch equals −9.

In addition, the homologues can be, for example, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NOs: 20-24 and 27-39, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example tetracycline-inducible promoter (Zabala M, et al., Cancer Res. 2004, 64(8): 2799-804).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed—i.e. mesenchymal stem cells.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMT010/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus Autographa californica nucleopolyhedrovirus (AcMNPV) as described in Liang C Y et al., 2004 (Arch Virol. 149: 51-60).

According to one embodiment, a lentiviral vector is used to transfect the mesenchymal stem cells.

Various methods can be used to introduce the expression vector of some embodiments of the invention into mesenchymal stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Other vectors can be used that are non-viral, such as cationic lipids, polylysine, and dendrimers. Nanoparticles are also contemplated.

Other modes of transfection that do not involved integration include the use of minicircle DNA vectors or the use of PiggyBac transposon that allows the transfection of genes that can be later removed from the genome.

As mentioned hereinabove, a variety of prokaryotic or eukaryotic cells can be used as host-expression systems to express the miRNAs of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV;

tobacco mosaic virus, TMV) or transformed with recombinant plasmid expression vectors, such as Ti plasmid, containing the coding sequence. Mammalian expression systems can also be used to express the miRNAs of some embodiments of the invention.

Examples of bacterial constructs include the pET series of *E. coli* expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

By determining the targets of the miRNAs of the present invention, it will be appreciated that the scope of the present invention may be broadened to include down-regulation of the targets by means other than contacting with miRNA.

For example, the present inventors have shown that one of the targets of miR-145 is connective tissue growth factor (CTGF). Thus the present invention contemplates that differentiation towards the oligodendrocytic lineage may be affected by down-regulation of this protein.

Thus, according to another aspect of the invention, there is provided a method of generating a population of cells useful for treating a CNS disorder in a subject, the method comprising contacting mesenchymal stem cells (MSCs) with an agent that downregulates an amount and/or activity of connective tissue growth factor (CTGF) or a receptor thereof, thereby generating the population of cells.

CTGF is a cysteine-rich monomeric peptide of $M_r$ 38,000. It is a member of the CCN family of growth regulators which includes the mouse (also known as fisp-12 or betaIG-M2) and human CTGF, Cyr61 (mouse), Cef10 (chicken), and Nov (chicken). Based on sequence comparisons, it has been suggested that the members of this family all have a modular structure, consisting of (1) an insulin-like growth factor domain responsible for binding, (2) a von Willebrand factor domain responsible for complex formation, (3) a thrombospondin type I repeat, possibly responsible for binding matrix molecules, and (4) a C-terminal module found in matrix proteins, postulated to be responsible for receptor binding.

The cDNA for human CTGF (hCTGF) has been reported to contain an open reading frame of 1047 nucleotides with an initiation site at position 130 and a TGA termination site at position 1177. The cDNA encodes a peptide of 349 amino acids. See, U.S. Patent Publ. US 2002/0115156A1. The cDNA sequence is also available at GenBank No.: NM_001901, which is also reproduced as SEQ ID NO: 25. The gene is reported to contain 2358 nucleotides with the open reading frame represented by nucleotides 207 through 1256. The 349 amino acid polypeptide expressed from this sequence is available under GenBank No.: NP_001892.1, which is also reproduced as SEQ ID NO: 26.

Downregulation of CTGF (or any of the other miRNA targets of the present invention) can be obtained at the genomic and/or the transcript level using a variety of molecules which interfere with transcription and/or translation (e.g., RNA silencing agents, Ribozyme, DNAzyme and antisense), or on the protein level using e.g., antagonists, enzymes that cleave the polypeptide and the like.

Following is a list of agents capable of downregulating expression level and/or activity of CTGF.

One example of an agent capable of downregulating CTGF is an antibody or antibody fragment capable of specifically binding thereto. Preferably, the antibody is capable of being internalized by the cell and entering the nucleus.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Downregulation of CTGF can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The present invention also contemplates introduction of long dsRNA specifically designed not to induce the interferon and PKR pathways for downregulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate dsRNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3'; (Brummelkamp, T. R. et al. (2002) Science 296: 550) and 5'-UUU-GUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA, as further described herein above.

Synthesis of RNA silencing agents suitable for use with the present invention can be effected as follows. First, the miRNA target mRNA sequence (e.g. CTGF sequence) is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambiondotcom/techlib/tn/91/912dothtml).

Second, potential target sites are compared to an appropriate genomic database (e.g., human, mouse, rat etc.) using any sequence alignment software, such as the BLAST software available from the NCBI server (wwwdotncbidotnlmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

The RNA silencing agents of the present invention may comprise nucleic acid analogs that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432: 173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIsl, TAT(48-60), pVEC, MTS, and MAP.

Another agent capable of downregulating CTGF is a DNAzyme molecule capable of specifically cleaving an mRNA transcript or DNA sequence of CTGF. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al.

Downregulation of CTGF can also be obtained by using an antisense polynucleotide capable of specifically hybridizing with an mRNA transcript encoding CTGF.

Design of antisense molecules which can be used to efficiently downregulate CTGF should take into consideration two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Another agent capable of downregulating CTGF is a ribozyme molecule capable of specifically cleaving an mRNA transcript encoding CTGF. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications.

An additional method of regulating the expression of a CTGF gene in cells is via triplex forming oligonuclotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Other agents which may be used to down-regulate CTGF are disclosed for example in US Patent Application No. 20080193443, incorporated herein by reference.

The conditions used for contacting the mesenchymal stem cells are selected for a time period/concentration of cells/concentration of miRNA/ratio between cells and miRNA which enable the miRNA to induce differentiation thereof. Likewise, the conditions used for contacting the mesenchymal stem cells are selected for a time period/concentration of cells/concentration of CTGF down-regulatory agent/ratio between cells and CTGF down-regulatory agent which enable the CTGF down-regulatory agent to induce differentiation thereof.

The present invention further contemplates incubation of the mesenchymal stem cells with a differentiation factor which promotes differentiation towards an oligodendrocytic lineage. The incubation with such differentiation factors may be affected prior to, concomitant with or following the contacting with the miRNA.

Alternatively, or additionally, the mesenchymal stem cells may be genetically modified so as to express such differentiation factors, using expression constructs such as those described herein above.

The present inventors showed that co-expression of at least one of the miRNAs disclosed herein and ciliary neurotrophic factor (CNTF), neurotrophin 3 (NT-3) or erythropoietin, increased the effects of the miRs beyond that effects of the miRs alone.

Additional contemplated differentiation factors include, but are not limited to heregulin, platelet derived growth factor (PDGF-AA) and tri-iodothyronine.

The differentiating factor may be a transcription factor, such as for example NKX2.2 and/or Olig2. The present inventors have shown that over-expression of one or both these transcription factors induce expression of oligodendrocyte markers (see FIG. 22).

The differentiating media may also comprise other agents such as neurotrophic factors (e.g. BDNF, GDNF, NTN, NT3 or LIF), hormones, growth factors (e.g. TGF-beta, TGF-alpha, and FGF), vitamins, hormones e.g., insulin, progesterone and other factors such as sonic hedgehog, bone morphogenetic proteins, forskolin, retinoic acid, ascorbic acid, putrescin, selenium and transferrin.

During or following the differentiation step the mesenchymal stem cells may be monitored for their differentiation state. Cell differentiation can be determined upon examination of cell or tissue-specific markers which are known to be indicative of differentiation. For example, the differentiated cells may express the following markers: GalC, O4, O1, CNPase, MOG and MBP.

Tissue/cell specific markers can be detected using immunological techniques well known in the art [Thomson J A et al., (1998). Science 282: 1145-7]. Examples include, but are not limited to, flow cytometry for membrane-bound markers, immunohistochemistry for extracellular and intracellular markers and enzymatic immunoassay, for secreted molecular markers.

In addition, cell differentiation can be also followed by specific reporters that are tagged with GFP or RFP and exhibit increased fluorescence upon differentiation.

Isolated cell populations obtained according to the methods describe herein are typically non-homogeneous.

The term "isolated" as used herein refers to a population of cells that has been removed from its in-vivo location (e.g. bone marrow, neural tissue). Preferably the isolated cell population is substantially free from other substances (e.g., other cells) that are present in its in-vivo location.

Cell populations may be selected such that more than about 50% of the cells express at least one, at least two, at least three, at least four, at least five or all of the following markers: GalC, O4, O1, CNPase, MOG and MBP.

Cell populations may be selected such that more than about 60% of the cells express at least one, at least two, at least three, at least four, at least five or all of the following markers: GalC, O4, O1, CNPase, MOG and MBP.

Cell populations may be selected such that more than about 70% of the cells express at least one, at least two, at least three, at least four, at least five or all of the following markers: GalC, O4, O1, CNPase, MOG and MBP.

Cell populations may be selected such that more than about 80% of the cells express at least one, at least two, at least three, at least four, at least five or all of the following markers: GalC, O4, O1, CNPase, MOG and MBP.

Cell populations may be selected such that more than about 90% of the cells express at least one, at least two, at least three, at least four, at least five or all of the following markers: GalC, O4, O1, CNPase, MOG and MBP.

Cell populations may be selected such that more than about 50% of the cells express at least one, at least two, at least three, at least four, at least five or all of the following markers: GalC, O4, O1, CNPase, MOG and MBP.

The cells of the populations of this aspect of the present invention may comprise structural oligodendrocyte phenotypes including a cell size, a cell shape, an organelle size and an organelle number. Thus, mature oligodendrocyte structural phenotypes include, a branched and ramified phenotype and formation of myelin membranes. Examples of oligodendrocyte progenitor cell (OPC) structural phenotype include, but are not limited to elongated, bipolar or multipolar morphology. For example only OPCs, but not mature oligodendrocytes, incorporate bromodeoxyuridine (BUdR), a hallmark of mitosis.

These structural phenotypes may be analyzed using microscopic techniques (e.g. scanning electro microscopy). Antibodies or dyes may be used to highlight distinguishing features in order to aid in the analysis.

The cells and cell populations of the present invention may be useful for a variety of therapeutic purposes. Diseases and conditions of the nervous system that result from the deterioration of, or damage to, the myelin sheathing generated by myelin producing cells are numerous. Myelin may be lost as a primary event due to direct damage to the myelin or as a secondary event as a result of damage to axons and neurons. Primary events include neurodegenerative diseases such as multiple sclerosis (MS), human immunodeficiency MS-associated myelopathy, transverse myelopathy/myelitis, progressive multi focal leukoencepholopathy, central pontine myelinolysis and lesions to the myelin sheathing (as described below for secondary events). Secondary events include a great variety of lesions to the axons or neurons caused by physical injury in the brain or spinal cord, ischemia diseases, malignant diseases, infectious diseases (such has HIV, Lyme disease, tuberculosis, syphilis, or herpes), degenerative diseases (such as Parkinson's, Alzheimer's, Huntington's, ALS, optic neuritis, postinfectious encephalomyelitis, adrenoleukodystrophy and adrenomyeloneuropathy), schizophrenia, nutritional diseases/disorders (such as folic acid and Vitamin B12 deficiency, Wernicke disease), systemic diseases (such as diabetes, systemic lupus erthematosis, carcinoma), and toxic substances (such as alcohol, lead, ethidium bromide); and iatrogenic processes such as drug interactions, radiation treatment or neurosurgery.

The use of differentiated MSCs may be also indicated for treatment of traumatic lesions of the nervous system including spinal cord injury and also for treatment of stroke caused by bleeding or thrombosis or embolism because of the need to induce neurogenesis and provide survival factors to minimize insult to damaged neurons.

Since differentiation of MSCs by miRs also induced the expression of various potent neurotrophic factors, the use of such cells may be indicated for treatment of all neurological diseases where providing neurotrophic factors may improve regeneration of injured neurons or enhance survival of damaged neurons.

In any of the methods described herein the cells may be obtained from an autologous, semi-autologous or non-autologous (i.e., allogeneic or xenogeneic) human donor or embryo or cord/placenta. For example, cells may be isolated from a human cadaver or a donor subject.

The term semi-autologous refers to donor cells which are partially-mismatched to recipient cells at a major histocompatibility complex (MHC) class I or class II locus.

The cells of the present invention can be administered to the treated individual using a variety of transplantation approaches, the nature of which depends on the site of implantation.

The term or phrase "transplantation", "cell replacement" or "grafting" are used interchangeably herein and refer to the introduction of the cells of the present invention to target tissue. As mentioned, the cells can be derived from the recipient or from an allogeneic, semi-allogeneic or xenogeneic donor.

The cells can be injected systemically into the circulation, administered intrathecally or grafted into the central nervous system, the spinal cord or into the ventricular cavities or subdurally onto the surface of a host brain. Conditions for successful transplantation include: (i) viability of the implant; (ii) retention of the graft at the site of transplantation; and (iii) minimum amount of pathological reaction at the site of transplantation. Methods for transplanting various nerve tissues, for example embryonic brain tissue, into host brains have been described in: "Neural grafting in the mammalian CNS", Bjorklund and Stenevi, eds. (1985); Freed et al., 2001; Olanow et al., 2003). These procedures include intraparenchymal transplantation, i.e. within the host brain (as compared to outside the brain or extraparenchymal transplantation) achieved by injection or deposition of tissue within the brain parenchyma at the time of transplantation.

Intraparenchymal transplantation can be performed using two approaches: (i) injection of cells into the host brain parenchyma or (ii) preparing a cavity by surgical means to expose the host brain parenchyma and then depositing the graft into the cavity. Both methods provide parenchymal deposition between the graft and host brain tissue at the time of grafting, and both facilitate anatomical integration between the graft and host brain tissue. This is of importance if it is required that the graft becomes an integral part of the host brain and survives for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord. The cells may also be introduced into the putamen, nucleus basalis, hippocampus cortex, striatum, substantia nigra or caudate regions of the brain, as well as the spinal cord.

The cells may also be transplanted to a healthy region of the tissue. In some cases the exact location of the damaged tissue area may be unknown and the cells may be inadvertently transplanted to a healthy region. In other cases, it may be preferable to administer the cells to a healthy region, thereby avoiding any further damage to that region. Whatever the case, following transplantation, the cells preferably migrate to the damaged area.

For transplanting, the cell suspension is drawn up into the syringe and administered to anesthetized transplantation recipients. Multiple injections may be made using this procedure.

The cellular suspension procedure thus permits grafting of the cells to any predetermined site in the brain or spinal cord, is relatively non-traumatic, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^9$ cells are introduced per graft. Cells can be administered concomitantly to different locations such as combined administration intrathecally and intravenously to maximize the chance of targeting into affected areas.

For transplantation into cavities, which may be preferred for spinal cord grafting, tissue is removed from regions close to the external surface of the central nerve system (CNS) to form a transplantation cavity, for example as described by Stenevi et al. (Brain Res. 114:1-20, 1976), by removing bone overlying the brain and stopping bleeding with a material such a gelfoam. Suction may be used to create the cavity. The graft is then placed in the cavity. More than one transplant may be placed in the same cavity using injection of cells or solid tissue implants. Preferably, the site of implantation is dictated by the CNS disorder being treated. Demyelinated MS lesions are distributed across multiple locations throughout the CNS, such that effective treatment of MS may rely more on the migratory ability of the cells to the appropriate target sites.

MSCs typically down regulate MHC class 2 and are therefore less immunogenic. Embryonal or newborn cells obtained from the cord blood, cord's Warton's gelly or placenta are further less likely to be strongly immunogenic and therefore less likely to be rejected, especially since such cells are immunosuppressive and immunoregulatory to start with.

Notwithstanding, since non-autologous cells may induce an immune reaction when administered to the body several approaches have been developed to reduce the likelihood of rejection of non-autologous cells. Furthermore, since diseases such as multiple sclerosis are inflammatory based diseases, the problem of immune reaction is exacerbated. These include either administration of cells to privileged sites, or alternatively, suppressing the recipient's immune system, providing anti-inflammatory treatment which may be indicated to control autoimmune disorders to start with and/or encapsulating the non-autologous/semi-autologous cells in immunoisolating, semipermeable membranes before transplantation.

As mentioned herein above, the present inventors also propose use of newborn mesenchymal stem cells to limit the immune reaction.

The following experiments may be performed to confirm the potential use of newborn's MSCs isolated from the cord/placenta for treatment of neurological disorders:

1) Differentiated MSCs (to various neural cells or neural progenitor cells) may serve as stimulators in one way mixed lymphocyte culture with allogeneic T cells and proliferative responses in comparison with T cells responding against allogeneic lymphocytes isolated from the same donor may be evaluated by $^3$H-Thymidine uptake to document hyporesponsiveness.
2) Differentiated MSCs may be added/co-cultured to one way mixed lymphocyte cultures and to cell cultures with T cell mitogens (phytohemmaglutinin and concanavalin A) to confirm the immunosuppressive effects on proliferative responses mediated by T cells.
3) Cord and placenta cells cultured from Brown Norway rats (unmodified and differentiated), may be enriched for MSCs and these cells may be infused into Lewis rats with induced experimental autoimmune encephalomyelitis (EAE). Alternatively, cord and placenta cells cultured from BALB/c mice, (BALB/c×C57BL/6)F1 or xenogeneic cells from Brown Norway rats (unmodified and differentiated), may be enriched for MSCs and these cells may be infused into C57BL/6 or SJL/j recipients with induced experimental autoimmune encephalomyelitis (EAE). The clinical effects against paralysis may be investigated to evaluate the therapeutic effects of xenogeneic, fully MHC mismatched or haploidentically mismatched MSCs. Such experiments may provide the basis for treatment of patients with a genetic disorder or genetically proned disorder with family member's haploidentical MSCs.
4) BALB/c MSCs cultured from cord and placenta may be transfused with pre-miR labeled with GFP or RFP, which will allow the inventors to follow the migration and persistence of these cells in the brain of C57BL/6 recipients with induced EAE. The clinical effects of labeled MHC mismatched differentiated MSCs may be evaluated by monitoring signs of disease, paralysis and histopathology. The migration and localization of such cells may be also monitored by using fluorescent cells from genetically transduced GFP "green" or Red2 "red" donors.

As mentioned, the present invention also contemplates encapsulation techniques to minimize an immune response.

Encapsulation techniques are generally classified as microencapsulation, involving small spherical vehicles and macroencapsulation, involving larger flat-sheet and hollowfiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylideneacetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 .mu.m. Such microcapsules can be further encapsulated with additional 2-5 .mu.m ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 .mu.m (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE™), etanercept, TNF alpha blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

In any of the methods described herein, the cells can be administered either per se or, preferably as a part of a pharmaceutical composition that further comprises a pharmaceutically acceptable carrier.

As used herein a "pharmaceutical composition" refers to a preparation of one or more of the cell compositions described herein, with other chemical components such as pharmaceutically suitable carriers and excipients. The purpose of a pharmaceutical composition is to facilitate administration of the cells to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration include direct administration into the circulation (intravenously or intra-arterial), into the spinal fluid or into the tissue or organ of interest. Thus, for example the cells may be administered directly into the brain.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. For example, animal models of demyelinating diseases include shiverer (shi/shi, MBP deleted) mouse, MD rats (PLP deficiency), Jimpy mouse (PLP mutation), dog shaking pup (PLP mutation), twitcher mouse (galactosylceramidase defect, as in human Krabbe disease), trembler mouse (PMP-22 deficiency). Virus induced demyelination model comprise use if Theiler's virus and mouse hepatitis virus. Autoimmune EAE is a possible model for multiple sclerosis.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1). For example, a multiple sclerosis patient can be monitored symptomatically for improved motor functions indicating positive response to treatment.

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively treat the brain disease/disorder. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated multiple sclerosis patient will be administered with an amount of cells which is sufficient to alleviate the symptoms of the disease, based on the monitoring indications.

The cells of the present invention may be co-administered with therapeutic agents useful in treating neurodegenerative disorders, such as gangliosides; antibiotics, neurotransmitters, neurohormones, toxins, neurite promoting molecules; and antimetabolites and precursors of neurotransmitter molecules such as L-DOPA. Additionally, the cells of the present invention may be co-administered with other cells capable of myelination—e.g. Schwann cells, such as those described in U.S. Pat. No. 6,989,271.

In addition to the ability of the different miRNAs to induce oligodendrocytic differentiation of MSCs, the present inventors have also found that the transfected MSCs can deliver the expressed miRs or pre-miRs to both glioma and neural stem cells, thus enabling their use in delivering miRs to endogenous cells in the brain.

Contemplated endogenous brain cells include neural cell, neural progenitor cell and/or cancer cells.

Thus, according to still another aspect of the present invention, there is provided a method of treating a nerve disease or disorder in a subject in need thereof, the method comprising:

(a) contacting a population of mesenchymal stem cells with at least one therapeutic miRNA, wherein said contacting is effected for less than 5 days; and (b) transplanting a therapeutically effective amount of said mesenchymal stem cells which have been modified to comprise said therapeutic miRNA to the brain of the subject, said miRNA being selected from the group consisting of SEQ ID NOs: miR-128, miR-9, miR9*, miR-124, miR137 and miR-218, thereby treating the nerve disease or disorder.

According to this aspect of the present invention the contacting is effected under conditions that does not allow neuronal or oligodendrocyte differentiation of the cells. Thus, for example the contact is effected in a medium that does not induce differentiation (e.g. DMEM (with fetal calf serum)) and for an amount of time that does not induce differentiation (e.g. less than 5 days, more preferably less than 4 days, more preferably less than 3 days, more preferably less than 2 and more preferably for about 1 day. The medium typically should not comprise additional factors which bring about the differentiation of the MSCs to neuronal or oligodendrocyte like cells—i.e. differentiation factors.

Thus, according to another aspect of the present invention there is provided a method of treating a brain tumor in a subject, the method comprising administering to the subject a therapeutically effective amount of mesenchymal stem cells which express (e.g. genetically modified to express) at least one of the following miRNAs: miR-145 (SEQ ID NO: 15), miR-124 (SEQ ID NO: 36), miR-137 (SEQ ID NO: 37), miR212 (SEQ ID NO: 29), miR-218 (SEQ ID NO: 38) and miR212 (SEQ ID NO: 39).

According to some embodiments the miRNA which is transported from MSCs to neural progenitor cells causes differentiation thereof. Such miRNAs include miRNA-124 (SEQ ID NO: 36), miR-9 (SEQ ID NO: 29), miR-9* (SEQ ID NO: 30), miR-137 (SEQ ID NO: 37) and miR 128 (SEQ ID NO: 18) and miR 218 (SEQ ID NO: 38).

The term "brain tumor" is not limited to any stage, grade, histomorphological feature, invasiveness, aggressivity or malignancy of an affected tissue or cell aggregation. In particular grade I, grade II, grade III or grade IV brain tumors, and all other types of cancers, malignancies and transformations associated with the brain are included. A preferred brain tumor to be treated by the method of the present invention is a glioma. Preferred are anaplastic astrocytomas, anaplastic oligoastrocytomas and anaplastic oligodendrogliomas, in particular fibrillary astrocytoma WHO grade II, oligoastrocytoma WHO grade II, oligodendroglioma grade II, anaplastic astrocytoma WHO grade III, anaplastic oligoastrocytoma WHO grade III, anaplastic oligodendroglioma grade III or glioblastoma.

The present inventors have found that co-expression of at least one of the miRNAs listed above and soluble TRAIL had a synergistic effect on apoptosis of the cancer cells. Thus, the present inventors contemplate co-expression of the miRNA and a pro-apoptotic agent in mesenchymal stem cells for the treatment of cancers, such as brain tumors.

As used herein, the phrase "pro-apoptotic agent" refers to an agent (e.g. chemical or polypeptide) capable of promoting programmed cell death.

Exemplary pro-apoptotic agents that may be used in accordance with the present invention include, but are not limited to TNF-α, FasL, Trail (Apo2 ligand) and Tweak (Apo3 ligand). Such pro-apoptotic agents may be recombinant polypeptides, biochemically synthesized or purified from cell extracts. Recombinant TNF-α, FasL, Trail and Tweak are all commercially available from Companies such as R&D Systems (Minneapolis, Minn.) and Abnova Corporation (Taiwan). Those skilled in the art are aware that many pharmaceutical agents exist that enhance apoptosis. Among such agents are bis-indolylmaleimide-8 and quabain. If desired, these agents may be used in conjunction with the proapoptotic agents of this invention.

As used herein the term "about" refers to +/−10%.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Mesenchymal Stromal Stem Cells:

Adult MSCs were obtained from 4 different sources, bone marrow, adipose tissue, umbilical cord (Wharton's jelly) and placenta.

Bone Marrow Aspiration:

After appropriate screening, painless bone marrow aspiration was performed under epidural anesthesia or systemic sedation and local infiltration with lignocaine 2% with puncture from the posterior superior iliac bone with the patient lying in left or right lateral position.

Obtaining Adipose Tissue Derived Mesenchymal Stem Cells:

Adipose tissue derived mesenchymal stem cells were isolated from liposuction either manually following separation of liquid fat followed by isolation of mononuclear cells from the fat tissue, or using Cytori cell separator using collagenase.

Preparation of MSCs:

A culture of purified mesenchymal stromal cells was prepared under aseptic conditions (positively pressurized "clean rooms") using filtered sterilized low glucose DMEM medium (Biological Industries) supplemented with 10% fetal bovine serum (Biological Industries), 1% L-glutamine (Biological Industries) and 1% penstrep-nystatin solution (Biological Industries). Mesenchymal cells were cultured for 24-48 days, until they reached confluence, and were then harvested and cryopreserved in 10% DMSO containing medium in liquid nitrogen (−196° C.). Most samples were harvested at passage 0, but cells maintained all the properties up to passage 4 with stable karyotype. A sample was taken for a 2 week sterility testing in the microbiological laboratory and for quality control. FACS analysis of the cells demonstrated that they consistently (more than 98%) expressed the characteristic MSC surface markers, CD29+, CD90+, CD105+, CD166+, and were negative for CD34, CD45 and CD14.

Neural Differentiation:

The cells were differentiated to the different neural cells using the protocols detailed below with and without the addition of various growth factors. Following the different treatments, the morphology of the cells, their growth pattern and survival are monitored daily using phase contrast microscopy, cell count, MTT and LDH assays. Different autophagy and apoptosis assays (e.g., LC3-II, acridine orange, Annexin/PI, active caspase 3) were also employed to detect cell death. No cell death was observed using any of the approaches used.

The differentiation of the cells was monitored by measuring the expression of various neural markers using immunofluorescence staining, Western blot analysis and real-time PCR. The following markers were tested:

Neural Progenitor Cells:

Nestin.

Neuronal:

βIII tubulin, MAP2, NeuroN.

The cells were also evaluated for the expression of neuronal excitability by the expression of the sodium channels NAV.1 and by assessing the electrophysiological characteristics of the cells.

Glial:

Astrocytic differentiation was characterized by the expression of GFAP and Oligodendrocytic differentiation was characterized by the expression of various markers indicative of the various stages of oligodendrocytes differentiation. Glial progenitors (GP) produce a bipolar morphology and begin to express Olig1, PDGFRa and NG2. Upon further culture and the addition of PDGF-AA, GPs begin to exhibit multiple filopodial extensions and begin to express O4 and later O1, GalC and CNPase. These OP cells were further characterized as early, mid- and late OP cells. Specifically, cells at the early OP stage began to express O4, while cells of the mid OP stage expressed O1 and GalC, and the late OP stage expressed CNPase. MOG and MBP were used as markers to indicate fully mature oligodendrocytes. Mature oligodendrocytes may be characterized by structural phenotype—large cell bodies and extensive filopodial branching.

Figure 1:
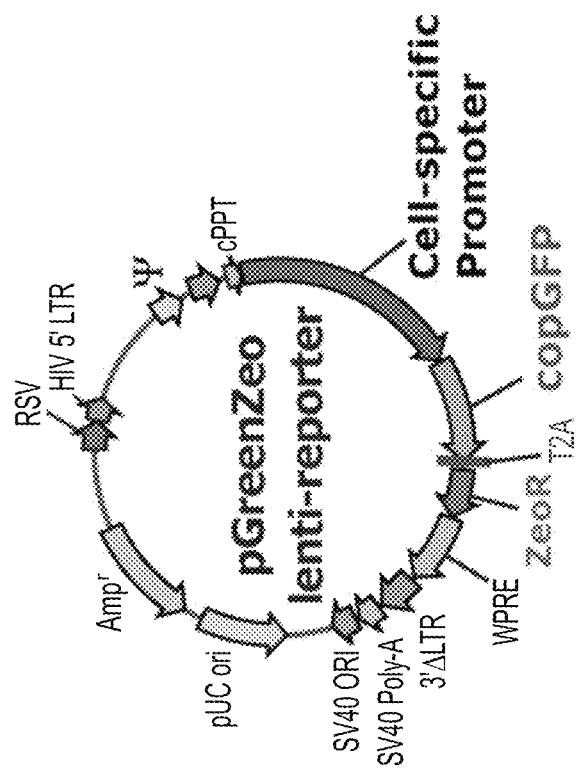

In a second approach, neural reporters were used for the high throughput analysis of MSC differentiation. Lentivirus vectors (see FIG. 1) expressing Nestin promoter-DsRed2, MAP2 promoter-GFP, GFAP promoter-GFP and MBP promoter-GFP were used, which allowed for the concomitant infection of the cells with markers of neural stem cells. The MSCs were infected with two reporters, (e.g. Nestin-DsRed2 and MAP2-GFP to assess neuronal differentiation, Nestin-DsRed2 and GFAP-GFP for astrocytic differentiation or Nestin-DsRed2 and MBP-GFP for oligodendrocytic differentiation) or the dsRed2 plasmid under the tyrosine hydroxylase promoter to assess dopaminergic differentiation. The level of differentiation was assessed by FACS analysis or confocal microscopy. This approach allows for the analysis of spatial and temporal differentiation in live cells and for the identification and purification of subpopulations of the differentiated MSCs.

Immunofluorescence Staining:

Cells were analyzed by immunofluorescence staining and were examined using an LSM510 Meta confocal microscope equipped with ultraviolet, argon, and helium/neon lasers (Nikon). The following primary antibodies were used: rabbit MAP2 (DAKO, Carpinteria, Calif.), mouse anti-β-III-tubulin (Covance, Richmond, Calif., 1:500) and rabbit anti-β-III-tubulin (Covance; 1:2000), rabbit anti-nestin and anti-O4 (Chemicon, 1:200) and anti-MOG (Chemicon 1:200). The secondary antibodies utilized were Alexa Fluor 488, 568, and 660 conjugated donkey immunoglobulin (MolecularProbesInc, Eugene, Oreg.).

Western Blot Analysis:

Cell pellets ($10^6$ cells/mL) were resuspended in 100 μL lysis buffer [25 mmol/L Tris-HCl (pH 7.4), 50 mmol/L NaCl, 0.5% Na deoxycholate, 2% % NP40, 0.2% SDS, 1 mmol/L PMSF, 50 μg/mL aprotinin, 50 μmol/L leupeptin, and 0.5 mmol/L $Na_3VO_4$] on ice for 15 minutes. Sample buffer (2×) was added and the samples were boiled for 5 minutes. Lysates (30 μg protein) were resolved by SDS-PAGE and transferred to nitrocellulose membranes. The membranes were blocked with 5% dry milk in PBS and subsequently stained with the primary antibody. Specific reactive bands were detected using a goat anti-rabbit or goat anti-mouse IgG conjugated to horseradish peroxidase (Bio-Rad, Hercules, Calif.) and the immunoreactive bands were visualized by the ECL Western blotting detection kit (Amersham, Arlington Heights, Ill.). Equal loading was verified by Ponceau S staining or by using anti-actin antibody.

Cell Transfection:

miRIDIAN microRNA mimics were obtained from Thermo Scientific. MSCs were transfected with miR-145, miR-125b or mir-128 or control miRNA using siMPORTER and after two days were transferred to NM medium containing G5. Similar results were obtained using pre-microRNA-145 expression vector (lentivirus vectors expressing pre-miR-145, System Biosciences).

Real-Time PCR:

Total RNA was extracted from the tissue samples by RNeasy (Qiagen) according to manufacturer's instructions. One microgram of total RNA was transcribed into cDNA using the Reverse Transcriptase System (Promega) and $pd(N)_6$ random nucleotides. Relative levels of the different oligodendrocyte-related mRNA were estimated by a semi-quantitative polymerase chain reaction (PCR) as compared to the mRNA levels of the ribosomal protein S-12. PCR amplification was performed using Taq DNA Polymerase (Takara, Japan). Amplification step consisted of 95° C. for 2 min and 26 or 30 (for S-12) cycles of 95° C. for 30 sec, 65° C. for 30 sec and 72° C. for 90 sec. In a preliminary study, each cDNA was amplified in serial of 20-40 cycles to obtain data within the linear-range of the assay. PCR products were size-fractionated by electrophoresis in 2% agarose gels and stained with ethidium bromide. The specificity of the PCR product was verified by DNA sequencing. Bands from RT-PCR using the specific oligo-related genes and S12 primers were scanned and quantified by Scion Image. The oligo-related gene products were normalized to S12 products to control for differences in loading and sample integrity.

The following primers were used: NKX2.2; forward 5'-GATGAAGTCTACCAAAGCTC (SEQ ID NO: 1) and reverse 5' AACTCCTTCTCCAGCTCTAG (SEQ ID NO: 2); OLIG2; forward 5' TTCAAGTCATCCTCGTCCAGC (SEQ ID NO: 3) and reverse 5' CTCGCGGCTGTTGATCTTGA (SEQ ID NO: 4); NG2; forward 5' TCTGACGGCGAGCACACTTC (SEQ ID NO: 5) and reverse 5' TCTGACTGCTGAGTG-GCTGG (SEQ ID NO: 6); CNPase; forward 5' TCAAGAAGGAGCTGCGACAAT (SEQ ID NO: 7) and reverse 5' AGCCTTCCCGTAGTCACAAA (SEQ ID NO: 8); PLP forward 5' TGATGCCAGAATGTATGGTGT (SEQ ID NO: 9) and reverse 5' GCAGCAATAAACAGGTGGAA (SEQ ID NO: 10) MBP; forward 5' AAGAACTGCTCAC-TACGGCTC (SEQ ID NO: 11) and reverse 5' AATCCTG-GTCTCTGGCCTTC (SEQ ID NO: 12). For S12 the following primers were employed: forward primer 5'-GGAAGGCATTGCTGCTGG (SEQ ID NO: 13), reverse primer: 5'-CCTCAATGACATCCTTGG (SEQ ID NO: 14; 285 bp product). Primers for S-12 and the different oligo-related genes span exon-intron junctions in order to avoid amplification of contaminating genomic DNA.

Luciferase Reporter Assay:

The 3' UTRs of CTGF in the pEZK-MO1 plasmid was transfected into BM-MSC followed by transfection with miR-145. After 72 hours, cell extract was obtained and firefly and *Renilla* luciferase activities were measured with the dual-luciferase reporter system (Promega) according to the manufacturer's instructions.

Example 1

Induction of Oligodendrocytic Differentiation by G5 Medium and miR-145

Results

G5 medium contains a mixture of insulin, hydrocortisone, transferrin and pyruvate. Incubation of the MSCs in G5 medium induced the generation of oligodendrocyte progenitor cells after 10-12 days in culture. After 6-8 days the cells started to exhibit bipolar morphology and to express markers of oligodendrocyte progenitor cells such as Olig1, Olig2 and NG2, whereas after 10-12 days the cells expressed higher levels of these markers (FIG. 3).

As presented in FIGS. 2A-B, the cells acquired bipolar morphology characteristics of early OPC.

To determine the effect of miR-145 on the differentiation of MSCs, three different preparations of the cells at passages 4-9 were employed. The cells were plated in DMEM+10% FCS for 24 hours and were then transfected with double-stranded RNA oligonucleotide of the mature sequence of miR-145 and with a negative control oligonucleotide. Following 2 days, cells were transferred to Neurobasal Medium (NB) supplemented with G5. Cell morphology was monitored every 24 hr and analysis of oligodendrocytic markers was determined following 12 days of transfection.

As presented in FIG. 4, transfection of the cells with miR-145 decreased cell proliferation and induced morphological differentiation of the cells already after 4 days of transfection. The cells acquired a typical oligodendrocytic phenotype with round cell bodies and multiple processes. Cells transfected with the control miRNA resembled the control untreated cells. About 80% of the miR-145 transfected cells exhibited oligodendrocytic morphology.

It was further found that transfection of the MSCs with miR-145 induced differentiation of the cells to more mature oligodendrocytic cells. After 12 days in cultures, the cells expressed markers such as GalC, O4, O1, high levels of CNPase mRNA and protein, expression of MOG and MBP mRNA. miR-145 induced oligodendrocytic differentiation in the majority of the treated MSCs.

Expression of GalC was detected by immunofluorescence staining in the treated cells (FIGS. 5A-D) and CNPase (FIG. 6) by Western blot analysis.

Growing the cells in G5 medium (without miRNA transfection) induced a small increase in CNPase, as compared to the NM (neuronal) medium and the effect of miR-145 was more significant in the G5 medium.

Real-Time PCR Analysis of Oligodendrocytic Markers:

The expression of various oligodendrocytic markers was analyzed using real-time PCR analysis. BM-MSCs were either incubated in oligodendrocytic medium (G5) or transfected with miR-145 and maintained in the same medium. As presented in FIG. 8, cells transfected with miR-145 in G5 medium induced the expression of different oligodendrocytic marker, in accordance with the results that are presented in FIG. 4.

Additional miRNAs were also analyzed for their effect on the expression of oligodendrocytic markers in MSCs maintained in G5 medium. The results are presented in FIG. 21. Similar results albeit to a different degree were observed with adipose MSCs (a similar or stronger effect), cord and placenta MSCs (data not shown). In addition to these miRs, it was also found that miR-26a, miR-196, miR9 and miR9* miR-10b, miR-25, miR-424, miR19 and miR149 induced oligodendrocytic markers when added in either G5 or NM media.

Overexpression of NKX2,2 and/or Olig2 were overexpressed in mesenchymal stem cells incubated in G5 medium. As presented in FIG. 22, overexpression of NKX2.2 increased the expression of the PDGFR alpha and induced a modest increase in the expression of CNPase. Overexpression of Olig2 induced an increase in the expression of PDGFRalpha, CNPase and proteolipid (PLP). In contrast, a larger increase was observed in the expression of all these markers by overexpression of Olig2 and NKX2.2 as well as in the staining of the immature oligodendrocyte marker O1.

MSCs Differentiated to Oligodendrocytes Lose their Mesenchymal Characteristics:

MSCs differentiate into osteoblasts, chondrocytes and adipocytes in response to appropriate stimuli. To examine the mesenchymal characteristics of the miR-differentiated MSCs two approaches were employed. In the first, the induced differentiation of these cells using specific staining for adipocytes, chondrocytes and osteoblasts was examined. A significant inhibition of differentiation towards the mesenchymal phenotypes was found in the miR-145, miR-125b or mir-128 transfected MSCs.

Example 2

MiR-145 Induces Oligodendrocytic Differentiation Also in Adipose-Derived MSCs

The effect of miR-145 on the oligodendrocytic differentiation of adipose derived MSCs was examined. Cells were transfected with 100 nM miR-145 or control miR and the cells were transferred to G5 medium. The morphological differentiation of the cells was determined following 12 days in culture. Similar to the BM-MSC, the adipose-derived MSCs also exhibited an oligodendrocytic differentiation following transfection with miR-145 (FIGS. 7A-F).

Example 3

Analysis of MSC Differentiation Using Specific Neural Reporters

Oligodendrocytic differentiation of BM-MSCs was analyzed using a specific fluorescent neural reporter, MBP-GFP. In this reporter the GFP is under the MBP promoter.

As presented in FIGS. 9A-B, transfection of the cells with miR-145 and incubation with G5 resulted in a oligodendrocytic differentiation and a large number of the treated MSCs were fluorescent indicating the induction of MBP in these cells.

Addition of T3 (tri-iodothyronine) or PDGF-AA to the miR-145 transfected cells, induced a more mature phenotype of the cells and some of them expressed MOG and MBP immunoreactivity.

Example 4

Connective Tissue Growth Factor (CTGF) is a Target of miR145 and Mediates its Effect on the Oligodendrocytic Differentiation of MSCs Targets of miR-145 were identified using several different sources of publicly-available software as each program uses its own unique algorithms to measure complementarity. To filter this extensive set of predicted targets, an Entrez Gene database search was conducted to only return proteins with reported roles in myelination and oligodendrocyte differentiation.

Using this approach, CTGF (connective tissue growth factor) was identified as a putative target of miR-145. To examine this possibility, the expression of CTGF mRNA and protein levels in MSCs transfected with miR-145 was examined. Cells were transfected with either miR-145 or control miR and the expression of CTGF was examined 3 days thereafter using real-time PCR. As presented in FIG. 11, miR-145 significantly decreased the expression of CTGF mRNA and protein.

In addition to demonstrating that miR-145 decreased the expression of CTGF the binding of miR-145 to the 3' UTR of CTGF was examined using a luciferase reporter assay. In this assay, the 3' UTR of CTGF was cloned into a luciferase reporter gene (FIG. 12).

This plasmid was transfected into MSCs and luciferase activity was quantified after 3 days. The cotransfection of miR-145 with the plasmid suppressed luciferase activity by about 70% (P<0.01) in comparison to a scrambled-duplex-cotransfected control (FIG. 13). These data indicate that the transfected miR-145 binds the target 3-UTR and repressed the expression of luciferase.

To examine the role of CTGF in the effect of miR-145 on oligodendrocytic differentiation, a CTGF construct that lacks the 3'-UTR of this gene was used. This CTGF construct partially abolished the oligodendrocytic differentiation induced by miR-145 suggesting that CTGF mediates, at least in part the oligodendrocytic differentiation induced by miR-145 (FIG. 14).

Example 5

Additional miRNAs Induce Oligodendrocytic Differentiation

In addition to miR-145 the present inventors have uncovered additional miRNAs that can induce oligodendrocytic differentiation.

Transfection of cord blood and BM-MSCs with miR-30d induced a 2.8 increase in CNPase mRNA and about 5-fold increase in MBP mRNA.

Similarly, miR-125b, miR-128 and miR-181c also increased the expression of various oligodendrocytic markers in BM-MSC and cord-MSC in G5 medium.

These miRs were also able to induce some neuronal differentiation in cells maintained in NM medium or in OptiMEM medium.

Example 6

MSCs can Deliver miRs to Neuronal Cells

Recent studies suggested that various cells, including MCSs can secrete miRs and that secreted miRs can be taken up by different cells. Since MSCs have been reported to migrate to sites of tumors and metastases in general and lesions including lesions in the brain and to areas of brain tumors, the present inventors examined whether MSCs can deliver exogenous pre-miRs and miRs to glioma cells and to neural stem cells. For these experiments MSCs were infected with lentivirus vector expressing pre-miR-145-GFP or with miR-145 as well as their respective controls, Con-pre-miR-GFP and Control miRNA. Transwells were used in which U87 glioma cells or human neural stem cells were plated in the lower wells and transfected MSCs were plated in the higher wells. After 24 and 48 hours, the supernatant and cells were collected and the levels of miRs and pre-miRs were determined. High levels of both pre-miR 145 and miR-145 were detected in the supernatants of the MSCs, suggesting that both the pre-MiR and miR can be secreted by the MSCs.

To further explore the ability of MSCs to deliver miRs, their ability to transfer miRs to glioma cells by co-culturing the two cell types together. For these experiments, U87 glioma cells were stained with a red dye and were co-cultured with MSCs transfected with a green fluorescent miR-145 and miR-124. Following 24-48 hr, the cells were viewed by a fluorescent microscope and the presence of the fluorescent miR-124 and miR-145 (green fluorescent) was monitored in the red fluorescent-labeled U87 cells. Since U87 cells do not express miR-145 or miR-124, the presence of these miRs in these cells resulted from their delivery by the co-cultured MSCs. Moreover, it was found that the level of CTGF, a target of miR-145 was decreased.

Finally, it was found that MSCs transfected with miR-124 and miR-145 significantly decreased the migration of U87 cells, when co-cultured together, as compared to MSCs transfected with a control miR. These results suggest that MSCs can secrete miRs, deliver it to adjacent cells and affect the function of the cells in a target-specific manner. Similar results were obtained in the human neural stem cells. These results suggest that following transfection into MSCs, miR-145 and miR-124 can serve to control differentiation of MSCs and the transfected cells themselves can be used to deliver these miRs to endogenous neural stem cells or oligodendrocyte precursor cells to induce their differentiation as well or to tumor cells to inhibit their growth and migration.

To examine the ability of MSCs to deliver miRNA to gliomas cells, MSCs from two different tissues were used—bone marrow and adipose, and two types of glioma cell lines, U87 and A172 were also used. In addition, two glioma stem cells (GSCs) derived from GBM specimens were also employed. In these experiments miRNAs that are not expressed in either the glioma cell lines or the GSCs were used. Recent studies indicated that miRNA-124 is expressed in low levels in GBMs. The present inventors therefore first examined the expression of this miRNA in glioma cell lines as compared to human astrocytes and in GSCs as compared to NSCs. Using qRT-PCR, it was found that miR-124 was not expressed in the different glioma cell lines or GSCs examined, whereas it was highly expressed in two types of NSCs and in human astrocytes. Similarly, it was found that miR-145 was not expressed in GSCs and in the glioma cells U87 and A172 (data not shown).

To examine the ability of MSCs to transfer exogenous miRNAs to glioma cells and GSCs, miR-124 and miR-145 mimics labeled with FAM or FITC were employed. The MSCs were transfected with the miR-124-FAM or miR-145-FITC and co-cultured with the specific glioma cell lines that were stained with CellTracker Red. Following 24 hour the cells were viewed under a confocal microscope.

Results

As presented in FIG. 15A, miR-124-FAM was observed in MSCs (green alone) and in some U87 cells labeled with the CellTracker Red. The same experiment was repeated with MSCs transfected with miR-145-FITC and similar results were obtained. The transfected MSCs efficiently transferred the miR-145 mimic into the adjacent co-cultured A172 glioma cells that were labeled with CellTracker Red (FIG. 15B).

To further demonstrate the delivery of miR mimics BM-MSCs were transfected with a non-fluorescent miR-145 mimic and these cells were co-cultured with CellTracker Red-labeled A172 cells. Following 24 hours, in situ hybridization of miR-145 in the glioma cells was performed. As presented in FIG. 16, the A172 cells that were co-cultured with MSCs expressing a control miRNA did not show expression of miR-145, whereas many of the A172 cells that were co-cultured with MSCs expressing the miR-145 mimic expressed this miR, further indicating that MSCs transfer exogenous miRs to neighboring glioma cells.

Example 7

Transferred MSC-Derived miR-124 Downregulates Gene Expression in Glioma Cells

The present inventors then examined if the transferred miR-124 was functional in glioma cells. miR-124 has been shown to target SCP-1 in various cells. qRT-PCR and a luciferase reporter assay was performed in order to determine whether the miR-124 mimic down-regulated expression of this gene in U87 cells. To examine the ability of the MSC-derived miR-124 mimic to target SCP-1 in the recipient glioma cells, the SCP-1 3'-UTR-luciferase plasmid was expressed in the U87 cells and luciferase activity in these cells co-cultured with MSCs transfected with a control miR or with miR-124 mimic was examined.

Results

Using qRT-PCR it was found that the miR-124 mimic down-regulated the expression of SCP-1 in U87 cells (FIG. 17A). The luciferase reporter assay showed that the miR-124 mimic significantly decreased the luciferase activity of this construct in these cells (FIG. 17B).

It was found that co-culture of U87 cells with BM-MSCs expressing a control miR did not affect the luciferase activity of the SCP-1 3'-UTR, whereas a co-culture of U87 with BM-MSCs expressing a miR-124 mimic resulted in a significant decrease (FIG. 17B). Similar results were observed with U87 cultured with AD-MSC expressing a miR-124 mimic (FIG. 17B). These results indicate that miR mimics are efficiently transferred by MSCs to the glioma cells and can downregulate the expression of their respective target genes.

Similar results were obtained using MSCs infected with pre-miR-124 plasmid tagged to GFP. The pre-miR was successfully transferred by the MSCs to the glioma cells, as evident by the significant decrease in the luciferase activity of the SCP-1 3'-UTR (data not shown).

Example 8

Transferred miR-124 Decreases the Migration of Glioma Cells

The present inventors next examined if the transferred miR-124 mimic can modulate the function of the glioma cells by analyzing their migration.

Results

It was found that transfection of glioma cells with a miR-124 mimic decreased the migration of these cells (FIG. 18A). Similarly, it was found that co-culture of U87 cells with MSCs transfected with a miR-124 mimic significantly decreased the migration of the cells as determined by a transwell migration assay and as compared with U87 cells cultured with MSCs expressing a control miR (FIGS. 18A, 4B).

Since the co-culture consisted of both MSCs and U87 cells, the present inventors further examined the specific migration of the U87 cells by analyzing only the Red tracker-labeled cells using a fluorescent microscope. As presented in FIGS. 18C and 18D, the U87 that were cultured with MSCs expressing a miR-124 mimic exhibited a significantly decreased cell migration as compared to cells cultured with MSCs expressing a control miR.

Similar results were obtained with AD-MSCs and with MSCs expressing a non fluorescent miR-124 (data not shown).

Example 9

MSCs Transfer miRs to GSCs and Regulate their Self-Renewal

Glioma stem cells (GSCs) are a rare population of cancer cells that play a role in the migration, resistance to therapy and recurrence of GBM. Therefore, targeting these cells is extremely important.

Results

It was found that BM-MSC and AD-BMCs successfully transferred miR-145-FITC to the HF-2584 GSCs, as evident by the localization of the fluorescent miR in the red labeled GSCs (FIG. 19A). In addition, it was found that miR-145 mimic decreased the self renewal of the HF2587 GSCs (FIG. 19B). Similarly, GSCs that were co-cultured with MSCs expressing a miR-145 mimic exhibited a significant decrease in their self-renewal as compared to GSCs that were co-cultured with MSCs expressing a control miR (FIG. 19B).

Furthermore, it was found that both BM-MSCs and AD-MSCs were able to transfer miR-124 mimic to the co-cultured HF-2584 GSCs as evident by the decrease luciferase activity of GSCs expressing the SCP-1 3-UTR tagged to luciferase (FIG. 19C).

Additional miRs and pre-miRs that could inhibit the growth of gliomas cells and the self-renewal of gliomas stem cells following transport in MSCs include miR-137 (SEQ ID NO: 37), miR-9 (SEQ ID NO: 29), miR-218 (SEQ ID NO: 38) and miR-212 (SEQ ID NO: 39).

It was found that some of the miRs transferred by the MSCs sensitized the gliomas cells and the gliomas stem cells to the apoptotic effect of TRAIL. Thus MSCs transfected with either miR-212 or miR 218 mimics or pre-miR 212 or pre miR-218, transferred the miR mimics or the mature miRs to co-cultured U87 and U251 glioma cells and to HF2684 and HF2303 GSCs and sensitized the cells 100 ng/ml TRAIL as compared to MSCs that expressed a control miR mimic or control pre-miR (data not shown).

Since MSCs can transfer miRs that sensitize glioma cells and glioma stem cells (GSCs) to TRAIL, lentivirus vectors were generated expressing both soluble TRAIL (sTRAIL) and pre-miR 212 or sTRAIL and pre-miR-218. When the MSCs were infected with lentivirus vectors expressing both sTRAIL and the specific pre-miRs they were both secreted. Co-culture of MSCs infected with lentivirus vector expressing either sTRAIL and pre-miR-212 or sTRAIL and pre-miR-218 significantly increased the apoptosis of the co-cultured U87, U251 and HF2303 and HF2584 GSCs as compared to MSCs infected with a control lentivirus vector or with lentivirus vectors expressing sTRAIL, pre-miR-212 or pre-miR-218 alone. These results suggest that MSCs can transfer efficiently both sTRAIL and specific pre-miRs to induce cell apoptosis in glioma cells and GSCs.

Example 10

MSCs Transfer Neuronal miRs to Neural Progenitor Cells and Promotes their Neuronal Differentiation In addition to transferring anti-cancer miR mimics to cancer cells, it was also found that MSCs were able to transfer neural miRs to neural progenitor cells. miR-124 has been shown to induce neuronal differentiation in neural progenitor cell and MSCs (WO2010144698).

The present inventors have now transfected MSCs with a miR-124 mimic and co cultured them with the neural progenitor cells RenCell labeled with CellTracker Red. Following 12 days in the co-culture the cells were stained for β3 tubulin-FITC and the percentage of the β3-tubulin positive cells was determined as compared to REN cells co-cultured with MSCs expressing a control miR.

Results

As presented in FIG. 20A, co-culturing of REN cells with MSCs expressing a miR-124 mimic significantly increased their neuronal differentiation as compared to REN cells co-cultured with MSCs expressing a control miR. In addition to the neuronal differentiation, it was found that the transferred miR-124 mimic decreased the luciferase activity of the SCP-1 3'-UTR-luciferase that was expressed in the RenCell (FIG. 20B).

Additional miR mimics and pre-miRs that were transferred successfully by MSCs to the neural progenitor cells which induced their neuronal differentiation, as indicated by an increase in β3-tubulin expression, include miR 9 (SEQ ID NO: 29), miR-9* (SEQ ID NO: 30), miR-137 (SEQ ID NO: 37) and miR 128 (SEQ ID NO: 18) and miR 218 (SEQ ID NO: 38).

In addition, it was also found that the MSCs transferred miR-145 mimic or premiR-145 to neural progenitor cells and induced their oligodendrocytic differentiation as indicated by the increased expression of CNPase and O1 (data not shown).

Example 11

Cord and Placenta-Derived MSCs Transfer miRs to Neighboring Cells

It was found that in addition to BM- and AD-derived MSCs, MSCs that are derived from cord or placenta were also able to transfer miR mimics and pre-miR to glioma cells and neural progenitor cells (data not shown).

Furthermore, it was found that the transfer of the miR mimics and pre-miRs by the different types of MSCs was mediated by exosomes (data not shown).

REFERENCES

1. Bradl M, Lassmann H. Oligodendrocytes: biology and pathology. Acta Neuropathol. 119:37-53, 2010.
2. Yun S J, Byun K, Bhin J, Oh J H, Nhung J H, Hwang D, Lee B. Transcriptional regulatory networks associated with self-renewal and differentiation of neural stem cells. J Cell Physiol. J Cell Physiol. 2010 Jul. 6. [Epub ahead of print].
3. Ash N S, Pitulescu M E, Kessel M. MicroRNAs in organogenesis and disease. Curr Mol Med. 8:698-710, 2008.
4. Kota S K, Balasubramanian S. Cancer therapy via modulation of micro RNA levels: a promising future. Drug Discov Today. J Cell Physiol. 2010 Jul. 6. [Epub ahead of print].
5. Mallanna S K, Rizzino A. Emerging roles of microRNAs in the control of embryonic stem cells and the generation of induced pluripotent stem cells. Dev Biol. 344:16-25, 2010.
6. Subramanian S, Steer C J. MicroRNAs as gatekeepers of apoptosis. J Cell Physiol. 223:289-98, 2010.
7. Meuleman N, Tondreau T, Ahmad I, Kwan J, Crokaert F, Delforge A, Dorval C, Martiat P, Lewalle P, Lagneaux L, Bron D. Infusion of mesenchymal stromal cells can aid hematopoietic recovery following allogeneic hematopoietic stem cell myeloablative transplant: a pilot study. Stem Cells Dev. 18(9): 1247-52, 2009.
8. Shi Y, Hu G, Su J, Li W, Chen Q, Shou P, Xu C, Chen X, Huang Y, Zhu Z, Huang X, Han X, Xie N, Ren G. Mesenchymal stem cells: a new strategy for immunosuppression and tissue repair. Cell Res. 20(5):510-8, 2010.
9. Kassis I, Grigoriadis N, Gowda-Kurkalli B, Mizrachi-Kol R, Ben-Hur T, Slavin S, Abramsky O, Karussis D. Neuroprotection and immunomodulation with mesenchymal stem cells in chronic experimental autoimmune encephalomyelitis. Arch Neurol. 65:753-761, 2008.
10. Le Blanc K, Frassoni F, Ball L, Locatelli F, Roelofs H, Lewis I, Lanino E, Sundberg B, Bernardo M E, Remberger M, Dini G, Egeler R M, Bacigalupo A, Fibbe W, Ringden O. Mesenchymal stem cells for treatment of steroid-resistant, severe, acute graft-versus-host disease: a phase II study. Lancet. 371(9624):1579-86, 2008.
11. Ramagopalan S V, Dobson R, Meier U C, Giovannoni G. Multiple sclerosis: risk factors, prodromes, and potential causal pathways. Lancet Neurol. 9:727-39, 2010.
12. Totoiu M O, Nistor G I, Lane T E, Keirstead H S. Remyelination, axonal sparing, and locomotor recovery following transplantation of glial-committed progenitor cells into the MHV model of multiple sclerosis. Exp. Neurol. 187:254-265, 2004.
13A. Erceg S, Ronaghi M, Oria M, Garcia Roselle M, Amparo Perez Arago M, Lopez M G, Radojevic I, Moreno-Manzano V, Rodriguez-Jimenez F J, Bhattacharya S S, Cordoba J, Stojkovic M. Transplanted Oligodendrocytes and Motoneuron Progenitors Generated from Human Embryonic Stem Cells Promote Locomotor Recovery After Spinal Cord Transection. Stem Cells. Stem Cells. 2010 Jul. 27. [Epub ahead of print].
13B. Karussis D, Karageorgiou C, Gowda-Kurkalli B, Vaknin-Dembinsky A, Gomori J M, Kassis I, Butte J, Ben-Hur T, Slavin S. Pilot Phase I/II clinical trial with autologous bone marrow derived mesenchymal stromal stem cells in patients with multiple sclerosis and amyotrophic lateral sclerosis. Presented at the AAI 2008. Archives of Neurology (in press).
14. Karussis D, Kassis I, Kurkalli B G, Slavin S Immunomodulation and neuroprotection with mesenchymal bone marrow stem cells (MSCs): a proposed treatment for multiple sclerosis and other neuroimmunological/neurodegenerative diseases. J Neurol Sci. 265(1-2):131-135, 2008.
15. Karussis D, Grigoriadis S, Polyzoidou E, Grigoriadis N, Slavin S, Abramsky O. Neuroprotection in multiple sclerosis. Clin Neurol Neurosurg. 108:250-254, 2006.
16. Slavin S, Kurkalli B G, Karussis D. The potential use of adult stem cells for the treatment of multiple sclerosis and other neurodegenerative disorders. Clin Neurol Neurosurg. 110:943-946, 2008.
17. Freedman M S, Bar-Or A, Atkins H L, Karussis D, Frassoni F, Lazarus H, Scolding N, Slavin S, Le Blanc K, Uccelli A. The therapeutic potential of mesenchymal stem cell transplantation as a treatment for multiple sclerosis: consensus report of the International MSCT Study Group. Mult Scler. 2010.
18. Wegner M. A matter of identity: transcriptional control in oligodendrocytes. J Mol Neurosci. 35:3-12, 2008.
19. Kennea N L, Waddington S N, Chan J, O'Donoghue K, Yeung D, Taylor D L, Al-Allaf F A, Pirianov G, Themis M, Edwards A D, Fisk N M, Mehmet H. Differentiation of human fetal mesenchymal stem cells into cells with an oligodendrocyte phenotype. Cell Cycle. 8:1069-1079, 2009.
20. Liu Z, Hu X, Cai J, Liu B, Peng X, Wegner M, Qiu M. Induction of oligodendrocyte differentiation by Olig2 and Sox10: evidence for reciprocal interactions and dosage-dependent mechanisms. Dev Biol. 302:683-693, 2007.
21. Fineberg S K, Kosik K S, Davidson B L. MicroRNAs potentiate neural development. Neuron. 64:303-309, 2009.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a brain tumor in a subject in need thereof, the method comprising transplanting a therapeutically effective amount of mesenchymal stem cells which have been modified to express exogenous miRNA miR-124, wherein said mesenchymal stem cells deliver said exogenous miRNA to the cytosol of a cell of the tumor, thereby treating the brain tumor.

2. The method of claim 1, wherein said brain tumor is a glioma.

3. The method of claim 1, further comprising expressing in said mesenchymal stem cells a pro-apoptotic agent.

4. The method of claim 3, wherein said pro-apoptotic agent comprises soluble TNF-related apoptosis-inducing ligand (sTRAIL).

* * * * *

```
SEQUENCE LISTING

<160> NUMBER OF SEQ ID NOS: 71

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
gatgaagtct accaaagctc                                               20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
aactccttct ccagctctag                                               20

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
ttcaagtcat cctcgtccag c                                             21

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
ctcgcggctg ttgatcttga                                               20

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
```
tctgacggcg agcacacttc                                                 20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
tctgactgct gagtggctgg                                                 20

<210> SEQ ID NO 7
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 7
tcaagaagga gctgcgacaa t                                               21

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
agccttcccg tagtcacaaa                                                 20

<210> SEQ ID NO 9
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 9
tgatgccaga atgtatggtg t                                               21

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
gcagcaataa acaggtggaa                                                 20

<210> SEQ ID NO 11
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 11
aagaactgct cactacggct c                                               21

<210> SEQ ID NO 12
<211> LENGTH: 20
<212> TYPE: DNA
<213> ORGANISM: Artificial sequence

```
<220> FEATURE:
<223> OTHER INFORMATION: Single strand DNA oligonucleotide

<400> SEQUENCE: 12
aatcctggtc tctggccttc                                                    20

<210> SEQ ID NO 13
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 13
ggaaggcatt gctgctgg                                                      18

<210> SEQ ID NO 14
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 14
cctcaatgac atccttgg                                                      18

<210> SEQ ID NO 15
<211> LENGTH: 23
<212> TYPE: RNA
<213> ORGANISM: Artificial sequence
<220> FEATURE:
<223> OTHER INFORMATION: miR-145

<400> SEQUENCE: 15
guccaguuuu cccaggaauc ccu                                                23

<210> SEQ ID NO 16
<211> LENGTH: 22
<212> TYPE: RNA
<213> ORGANISM: Artificial sequence
<220> FEATURE:
<223> OTHER INFORMATION: miR-30d

<400> SEQUENCE: 16
uguaaacauc cccgacugga ag                                                 22

<210> SEQ ID NO 17
<211> LENGTH: 22
<212> TYPE: RNA
<213> ORGANISM: Artificial sequence
<220> FEATURE:
<223> OTHER INFORMATION: miR-125b

<400> SEQUENCE: 17
ucccugagac ccuaacuugu ga                                                 22

<210> SEQ ID NO 18
<211> LENGTH: 21
<212> TYPE: RNA
<213> ORGANISM: Artificial sequence
<220> FEATURE:
<223> OTHER INFORMATION: miR-128

<400> SEQUENCE: 18
ucacagugaa ccggucucuu u                                                  21
```

```
<210> SEQ ID NO 19
<211> LENGTH: 22
<212> TYPE: RNA
<213> ORGANISM: Artificial sequence
<220> FEATURE:
<223> OTHER INFORMATION: miR-181c

<400> SEQUENCE: 19
aacauucaac cugucgguga gu                                             22

<210> SEQ ID NO 20
<211> LENGTH: 308
<212> TYPE: DNA
<213> ORGANISM: Artificial sequence
<220> FEATURE:
<223> OTHER INFORMATION: Pre-miR145 precursor sequence

<400> SEQUENCE: 20
tcgaggatcc gcaccccacc ctggctgcta cagatggggc tggatgcaga agagaactcc    60
agctggtcct tagggacacg gcggccttgg cgctgaaggc cactcgctcc caccttgtcc   120
tcacggtcca gttttcccag gaatcccttg atgctaaga tggggattcc tggaaatact    180
gttcttgagg tcatggtttc acagctggat ttgcctcctt cccacccccac agttgccccc  240 caatggggcc tcggctggct cacaggatga gggttcaaga agaaggctgt ccctggaggc   300
tagctcga                                                           308

<210> SEQ ID NO 21
<211> LENGTH: 290
<212> TYPE: DNA
<213> ORGANISM: Artificial sequence
<220> FEATURE:
<223> OTHER INFORMATION: Pre-miR30d precursor sequence

<400> SEQUENCE: 21
tcgaggatcc tattgttcag cactagaaat tatataaatt attagctgaa gatgatgact    60
ggcaacattt atgtctgttc ctcctcttaa atttcttgtt cagaaagtct gttgttgtaa   120
acatccccga ctggaagctg taagacacag ctaagctttc agtcagatgt ttgctgctac   180
cggctattca cagacatcct cttgatataa ttctgtcccg gagtggagtt gaggaggcta   240
taaaatgtgt gggaaaacct cagaaatctt tagctgcatt gctagctcga              290

<210> SEQ ID NO 22
<211> LENGTH: 309
<212> TYPE: DNA
<213> ORGANISM: Artificial sequence
<220> FEATURE:
<223> OTHER INFORMATION: Pre-miR125b precursor sequence

<400> SEQUENCE: 22
tcgaggatcc tgaagtattt taaatagtat ttagaggtaa aagtctaagt gaacccaact    60
gtaatttcta agctatcctt atttctggaa gaagaattct accgcatcaa accagacttt   120
tcctagtccc tgagacccta acttgtgagg tattttagta acatcacaag tcaggctctt   180
gggacctagg cggaggggaa ccagcagctt tggaccttat tgattgtctg cagttaccac   240
cagaacaaaa gaacatacat agattctgcc taggagaaaa gaacaatgct tttctttatg   300
ctagctcga                                                          309

<210> SEQ ID NO 23
<211> LENGTH: 332
```

<212> TYPE: DNA
<213> ORGANISM: Artificial sequence
<220> FEATURE:
<223> OTHER INFORMATION: Pre-miR128 precursor sequence

<400> SEQUENCE: 23

| | | | | | | |
|---|---|---|---|---|---|---|
| tcgaggatcc | ttacaaagcc | ctagctgttt | tctgtgtagc | ttttattatt | cttatgactc | 60 |
| ttgacaagtt | tgtagcttca | ccatatacat | ttaatatttt | gcaataattg | gccttgttcc | 120 |
| tgagctgttg | gattcggggc | cgtagcactg | tctgagaggt | ttacatttct | cacagtgaac | 180 |
| cggtctcttt | ttcagctgct | tcctggcttc | tttttactca | ggtttccact | gcttttttgc | 240 |
| ttttttttaat | gctgtatgaa | ggtgttaaca | tttgtttata | ttttttcatta | attgtaatac | 300 |
| ctttaaatca | tgcatcatac | tcgctagctc | ga | | | 332 |

<210> SEQ ID NO 24
<211> LENGTH: 110
<212> TYPE: DNA
<213> ORGANISM: Artificial sequence
<220> FEATURE:
<223> OTHER INFORMATION: Pre-miR181c precursor sequence

<400> SEQUENCE: 24

| | | | | | | |
|---|---|---|---|---|---|---|
| cggaaaattt | gccaagggtt | tgggggaaca | ttcaacctgt | cggtgagttt | gggcagctca | 60 |
| ggcaaaccat | cgaccgttga | gtggaccctg | aggcctggaa | ttgccatcct | | 110 |

<210> SEQ ID NO 25
<211> LENGTH: 2358
<212> TYPE: DNA
<213> ORGANISM: Homo sapiens

<400> SEQUENCE: 25

| | | | | | | |
|---|---|---|---|---|---|---|
| aaactcacac | aacaactctt | ccccgctgag | aggagacagc | cagtgcgact | ccaccctcca | 60 |
| gctcgacggc | agccgccccg | gccgacagcc | ccgagacgac | agcccggcgc | gtcccggtcc | 120 |
| ccacctccga | ccaccgccag | cgctccaggc | cccgccgctc | cccgctcgcc | gccaccgcgc | 180 |
| cctccgctcc | gcccgcagtg | ccaaccatga | ccgccgccag | tatgggcccc | gtccgcgtcg | 240 |
| ccttcgtggt | cctcctcgcc | ctctgcagcc | ggccggccgt | cggccagaac | tgcagcgggc | 300 |
| cgtgccggtg | cccggacgag | ccggcgccgc | gctgcccggc | gggcgtgagc | ctcgtgctgg | 360 |
| acggctgcgg | ctgctgccgc | gtctgcgcca | agcagctggg | cgagctgtgc | accgagcgcg | 420 |
| accccctgcga | cccgcacaag | ggcctcttct | gtgacttcgg | ctccccggcc | aaccgcaaga | 480 |
| tcggcgtgtg | caccgccaaa | gatggtgctc | cctgcatctt | cggtggtacg | gtgtaccgca | 540 |
| gcggagagtc | cttccagagc | agctgcaagt | accagtgcac | gtgcctggac | ggggcggtgg | 600 |
| gctgcatgcc | cctgtgcagc | atggacgttc | gtctgcccag | ccctgactgc | ccttcccga | 660 |
| ggagggtcaa | gctgcccggg | aaatgctgcg | aggagtgggt | gtgtgacgag | cccaaggacc | 720 |
| aaaccgtggt | tgggcctgcc | ctcgcggctt | accgactgga | agacacgttt | ggcccagacc | 780 |
| caactatgat | tagagccaac | tgcctggtcc | agaccacaga | gtggagcgcc | tgttccaaga | 840 |
| cctgtgggat | gggcatctcc | acccgggtta | ccaatgacaa | cgcctcctgc | aggctagaga | 900 |
| agcagagccg | cctgtgcatg | gtcaggcctt | gcgaagctga | cctggaagag | aacattaaga | 960 |
| agggcaaaaa | gtgcatccgt | actcccaaaa | tctccaagcc | tatcaagttt | gagctttctg | 1020 |
| gctgcaccag | catgaagaca | taccgagcta | aattctgtgg | agtatgtacc | gacgccgat | 1080 |
| gctgcaccc | ccacagaacc | accaccctgc | cggtggagtt | caagtgccct | gacggcgagg | 1140 |

```
tcatgaagaa gaacatgatg ttcatcaaga cctgtgcctg ccattacaac tgtcccggag    1200
acaatgacat ctttgaatcg ctgtactaca ggaagatgta cggagacatg gcatgaagcc    1260
agagagtgag agacattaac tcattagact ggaacttgaa ctgattcaca tctcattttt    1320
ccgtaaaaat gatttcagta gcacaagtta tttaaatctg tttttctaac tgggggaaaa    1380
gattcccacc caattcaaaa cattgtgcca tgtcaaacaa atagtctatc aaccccagac    1440
actggtttga agaatgttaa gacttgacag tggaactaca ttagtacaca gcaccagaat    1500
gtatattaag gtgtggcttt aggagcagtg ggagggtacc agcagaaagg ttagtatcat    1560
cagatagcat cttatacgag taatatgcct gctatttgaa gtgtaattga aaggaaaat     1620 tttagcgtgc tcactgacct gcctgtagcc ccagtgacag ctaggatgtg cattctccag    1680
ccatcaagag actgagtcaa gttgttcctt aagtcagaac agcagactca gctctgacat    1740
tctgattcga atgacactgt tcaggaatcg gaatcctgtc gattagactg gacagcttgt    1800
ggcaagtgaa tttgcctgta caagccaga ttttttaaaa tttatattgt aaatattgtg     1860
tgtgtgtgtg tgtgtgtata tatatatata tgtacagtta tctaagttaa tttaaagttg    1920
tttgtgcctt tttattttg ttttaatgc tttgatattt caatgttagc ctcaatttct      1980
gaacaccata ggtagaatgt aaagcttgtc tgatcgttca aagcatgaaa tggatactta    2040 tatgaaatt ctgctcagat agaatgacag tccgtcaaaa cagattgttt gcaaagggga     2100
ggcatcagtg tccttggcag gctgatttct aggtaggaaa tgtggtagcc tcactttaa     2160 tgaacaaatg gcctttatta aaaactgagt gactctatat agctgatcag ttttttcacc   2220
tggaagcatt tgtttctact ttgatatgac tgtttttcgg acagtttatt tgttgagagt    2280
gtgaccaaaa gttacatgtt tgcacctttc tagttgaaaa taaagtgtat attttttcta    2340
taaaaaaaaa aaaaaaaa                                                  2358

<210> SEQ ID NO 26
<211> LENGTH: 349
<212> TYPE: PRT
<213> ORGANISM: Homo sapiens

<400> SEQUENCE: 26

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
                20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160
```

```
Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Leu Pro Val Glu
    290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345

<210> SEQ ID NO 27
<211> LENGTH: 22
<212> TYPE: RNA
<213> ORGANISM: Homo sapiens
<220> FEATURE:
<221> NAME/KEY: misc_feature
<223> OTHER INFORMATION: miR-26a

<400> SEQUENCE: 27
uucaaguaau ccaggauagg cu                                              22

<210> SEQ ID NO 28
<211> LENGTH: 22
<212> TYPE: RNA
<213> ORGANISM: Homo sapiens
<220> FEATURE:
<221> NAME/KEY: misc_feature
<223> OTHER INFORMATION: miR-196

<400> SEQUENCE: 28
uagguaguuu cauguuguug gg                                              22

<210> SEQ ID NO 29
<211> LENGTH: 23
<212> TYPE: RNA
<213> ORGANISM: Homo sapiens
<220> FEATURE:
<221> NAME/KEY: misc_feature
<223> OTHER INFORMATION: miR9

<400> SEQUENCE: 29
ucuuugguua ucuagcugua uga                                             23

<210> SEQ ID NO 30
<211> LENGTH: 23
```

```
<212> TYPE: RNA
<213> ORGANISM: Homo sapiens
<220> FEATURE:
<221> NAME/KEY: misc_feature
<223> OTHER INFORMATION: miR9*

<400> SEQUENCE: 30
ucuuugguua ucuagcugua uga                                               23

<210> SEQ ID NO 31
<211> LENGTH: 23
<212> TYPE: RNA
<213> ORGANISM: Homo sapiens
<220> FEATURE:
<221> NAME/KEY: misc_feature
<223> OTHER INFORMATION: miR-10b

<400> SEQUENCE: 31
uacccuguag aaccgaauuu gug                                               23

<210> SEQ ID NO 32
<211> LENGTH: 22
<212> TYPE: RNA
<213> ORGANISM: Homo sapiens
<220> FEATURE:
<221> NAME/KEY: misc_feature
<223> OTHER INFORMATION: miR-25

<400> SEQUENCE: 32
cauugcacuu gucucggucu ga                                                22

<210> SEQ ID NO 33
<211> LENGTH: 22
<212> TYPE: RNA
<213> ORGANISM: Homo sapiens
<220> FEATURE:
<221> NAME/KEY: misc_feature
<223> OTHER INFORMATION: miR-424

<400> SEQUENCE: 33
cagcagcaau ucauguuuug aa                                                22

<210> SEQ ID NO 34
<211> LENGTH: 23
<212> TYPE: RNA
<213> ORGANISM: Homo sapiens
<220> FEATURE:
<221> NAME/KEY: misc_feature
<223> OTHER INFORMATION: miR-19

<400> SEQUENCE: 34
ugugcaaauc uaugcaaaac uga                                               23

<210> SEQ ID NO 35
<211> LENGTH: 23
<212> TYPE: RNA
<213> ORGANISM: Homo sapiens
<220> FEATURE:
<221> NAME/KEY: misc_feature
<223> OTHER INFORMATION: miR149

<400> SEQUENCE: 35
ucuggcuccg ugucuucacu ccc                                               23

<210> SEQ ID NO 36
<211> LENGTH: 20
<212> TYPE: RNA
```

-continued

```
<213> ORGANISM: Homo sapiens
<220> FEATURE:
<221> NAME/KEY: misc_feature
<223> OTHER INFORMATION: miR124

<400> SEQUENCE: 36
uaaggcacgc ggugaaugcc                                               20

<210> SEQ ID NO 37
<211> LENGTH: 23
<212> TYPE: RNA
<213> ORGANISM: Homo sapiens
<220> FEATURE:
<221> NAME/KEY: misc_feature
<223> OTHER INFORMATION: miR137

<400> SEQUENCE: 37
uuauugcuua agaauacgcg uag                                           23

<210> SEQ ID NO 38
<211> LENGTH: 21
<212> TYPE: RNA
<213> ORGANISM: Homo sapiens
<220> FEATURE:
<221> NAME/KEY: misc_feature
<223> OTHER INFORMATION: miR218

<400> SEQUENCE: 38
uugugcuuga ucuaaccaug u                                             21

<210> SEQ ID NO 39
<211> LENGTH: 21
<212> TYPE: RNA
<213> ORGANISM: Homo sapiens
<220> FEATURE:
<221> NAME/KEY: misc_feature
<223> OTHER INFORMATION: miR212

<400> SEQUENCE: 39
uaacagucuc cagucacggc c                                             21

<210> SEQ ID NO 40
<211> LENGTH: 2095
<212> TYPE: DNA
<213> ORGANISM: Homo sapiens

<400> SEQUENCE: 40
gcggccgccg gagcccgagc tgacgccgcc ttggcacccc tcctggagtt agaaactaag    60
gccggggccc gcggcgctcg gcgcgcaggc cgccggcctt cctgcgtcca tttccgcgtg   120
cttccaaaga agacagagag aggcactggg ttgggcttca ttttttttcct ccccatcccc  180 agtttctttc tcttttttaaa aataataatt atcccaataa ttaaagccaa ttccccctc   240 ccctccccca gtccctcccc ccaactcccc cctccccgc ccgccggggc aggggagcgc    300
cacgaattga ccaagtgaag ctacaacttt gcgacataaa ttttgggtc tcgaaccatg    360 tcgctgacca acacaaagac ggggttttcg gtcaaggaca tcttagacct gccggacacc    420
aacgatgagg agggctctgt ggccgaaggt ccggaggaag agaacgaggg gcccgagcca    480
gccaagaggg ccgggccgct ggggcagggc gccctggacg cggtgcagag cctgccctg     540 aagaacccct tctacgacag cagcgacaac ccgtacacgc gctggctggc cagcaccgag    600
ggccttcagt actccctgca cggtctggct gccggggcgc ccctcagga ctcaagctcc     660 aagtccccgg agccctcggc cgacgagtca ccggacaatg acaaggagac cccgggcggc    720
```

```
gggggggacg ccggcaagaa gcgaaagcgg cgagtgcttt tctccaaggc gcagacctac      780
gagctggagc ggcgctttcg gcagcagcgg tacctgtcgg cgcccgagcg cgaacacctg      840
gccagcctca tccgcctcac gcccacgcag gtcaagatct ggttccagaa ccaccgctac      900
aagatgaagc gcgcccgggc cgagaaaggt atggaggtga cgcccctgcc ctcgccgcgc      960
cgggtggccg tgcccgtctt ggtcagggac ggcaaaccat gtcacgcgct caaagcccag     1020
gacctggcag ccgccacctt ccaggcgggc attccctttt ctgcctacag cgcgcagtcg     1080
ctgcagcaca tgcagtacaa cgcccagtac agctcggcca gcaccccca gtacccgaca     1140 gcacaccccc tggtccaggc ccagcagtgg acttggtgag cgccgcccca acgagactcg     1200
cggccccagg cccaggcccc acccggcgg cggtggcggc gaggaggcct cggtccttat     1260
ggtggttatt attattatta taattattat tatggagtcg agttgactct cggctccact     1320
agggaggcgc cgggaggttg cctgcgtctc cttggagtgg cagattccac ccacccagct     1380
ctgcccatgc ctctccttct gaaccttggg agagggctga actctacgcc gtgtttacag     1440
aatgtttgcg cagcttcgct tctttgcctc tccccggggg gaccaaaccg tcccagcgtt     1500
aatgtcgtca cttgaaaacg agaaaaagac cgaccccca cccctgcttt cgtgcatttt     1560
gtaaaatatg tttgtgtgag tagcgatatt gtcagccgtc ttctaaagca agtggagaac     1620
actttaaaaa tacagagaat ttcttccttt ttttaaaaaa aaataagaaa atgctaaata     1680
tttatggcca tgtaaacgtt ctgacaactg gtggcagatt tcgcttttcg ttgtaaatat     1740
cggtggtgat tgttgccaaa atgaccttca ggaccggcct gtttcccgtc tgggtccaac     1800
tcctttcttt gtggcttgtt tgggtttgtt ttttgttttg ttttgttttt tgcgttttcc     1860
cctgctttct tcctttctct ttttattta ttgtgcaaac atttctcaaa tatggaaaag     1920
aaaaccctgt aggcagggag ccctctgccc tgtcctccgg gccttcagcc ccgaacttgg     1980
agctcagcta ttcggcgcgg ttccccaaca gcgccgggcg cagaaagctt tcgatttttt     2040
aaataagaat tttaataaaa atcctgtgtt taaaaagaa aaaaaaaaa aaaaa          2095
```

<210> SEQ ID NO 41
<211> LENGTH: 2505
<212> TYPE: DNA
<213> ORGANISM: Homo sapiens

<400> SEQUENCE: 41

```
gtgcggatgc ttattataga tcgacgcgac accagcgccc ggtgccaggt tctcccctga       60
ggcttttcgg agcgagctcc tcaaatcgca tccagatttt cgggtccgag ggaaggagga      120
ccctgcgaaa gctgcgacga ctatcttccc ctggggccat ggactcggac gccagcctgg      180
tgtccagccg cccgtcgtcg ccagagcccg atgaccttt tctgccggcc cggagtaagg      240
gcagcagcgg cagcgccttc actggggca ccgtgtcctc gtccaccccg agtgactgcc      300
cgccggagct gagcgccgag ctgcgcggcg ctatgggctc tgcgggcgcg catcctgggg      360
acaagctagg aggcagtggc ttcaagtcat cctcgtccag cacctcgtcg tctacgtcgt      420
cggcggctgc gtcgtccacc aagaaggaca agaagcaaat gacagagccg gagctgcagc      480
agctgcgtct caagatcaac agccgcgagc gcaagcgcat gcacgacctc aacatcgcca      540
tggatggcct ccgcgaggtc atgccgtacg cacacggccc ttcggtgcgc aagctttcca      600
agatcgccac gctgctgctg gcgcgcaact acatcctcat gctcaccaac tcgctggagg      660
agatgaagcg actggtgagc gagatctacg ggggccacca cgctggcttc caccccgtcgg     720
```

```
cctgcggcgg cctggcgcac tccgcgcccc tgcccgccgc caccgcgcac ccggcagcag    780
cagcgcacgc cgcacatcac cccgcggtgc accaccccat cctgccgccc gccgccgcag    840
cggctgctgc cgccgctgca gccgcggctg tgtccagcgc ctctctgccc ggatccgggc    900
tgccgtcggt cggctccatc cgtccaccgc acggcctact caagtctccg tctgctgccg    960
cggccgcccc gctgggggggc ggggcggcg gcagtggggc gagcgggggc ttccagcact    1020
ggggcggcat gccctgcccc tgcagcatgt gccaggtgcc gccgccgcac caccacgtgt    1080
cggctatggg cgccggcagc ctgccgcgcc tcacctccga cgccaagtga gccgactggc    1140
gccggcgcgt tctggcgaca ggggagccag gggccgcggg gaagcgagga ctggcctgcg    1200
ctgggctcgg gagctctgtc gcgaggaggg gcgcaggacc atggactggg ggtggggcat    1260
ggtggggatt ccagcatctg cgaacccaag caatggggcc gcccacagag cagtggggag    1320
tgaggggatg ttctctccgg gacctgatcg agcgctgtct ggctttaacc tgagctggtc    1380
cagtagacat cgttttatga aaggtaccg ctgtgtgcat tcctcactag aactcatccg    1440
acccccgacc cccacctccg ggaaaagatt ctaaaaactt ctttccctga gagcgtggcc    1500
tgacttgcag actcggcttg ggcagcactt cgggggggga ggggtgtta tgggaggggg    1560 acacattggg gccttgctcc tcttcctcct ttcttggcgg gtgggagact ccgggtagcc    1620
gcactgcaga agcaacagcc cgaccgcgcc ctccagggtc gtccctggcc caaggccagg    1680
ggccacaagt tagttggaag ccggcgttcg gtatcagaag cgctgatggt catatccaat    1740
ctcaatatct gggtcaatcc acaccctctt agaactgtgg ccgttcctcc ctgtctctcg    1800
ttgatttggg agaatatggt tttctaataa atctgtggat gttccttctt caacagtatg    1860
agcaagttta tagacattca gagtagaacc acttgtggat tggaataacc caaaactgcc    1920
gatttcaggg gcgggtgcat tgtagttatt attttaaaat agaaactacc ccaccgactc    1980
atctttcctt ctctaagcac aaagtgattt ggttattttg gtacctgaga acgtaacaga    2040
attaaaaggc agttgctgtg gaaacagttt gggttatttg ggggttctgt tggcttttta    2100
aaattttctt tttggatgt gtaaatttat caatgatgag gtaagtcgcg aatgctaagc    2160
tgtttgctca cgtgactgcc agccccatcg gagtctaagc cggctttcct ctattttggt    2220 ttattttgc cacgtttaac acaaatggta aactcctcca cgtgcttcct gcgttccgtg    2280
caagccgcct cggcgctgcc tgcgttgcaa actgggcttt gtagcgtctg ccgtgtaaca    2340
cccttcctct gatcgcaccg cccctcgcag agagtgtatc atctgtttta tttttgtaaa    2400
aacaaagtgc taaataatat ttattacttg tttggttgca aaaacggaat aaatgactga    2460
gtgttgagat tttaaataaa atttaaagca aaaaaaaaaa aaaaa                    2505
```

<210> SEQ ID NO 42
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-302a

<400> SEQUENCE: 42
uaagugcuuc cauguuuugg uga                                              23

<210> SEQ ID NO 43
<211> LENGTH: 69
<212> TYPE: RNA
<213> ORGANISM: Homo sapiens
<220> FEATURE:

<221> NAME/KEY: misc_feature
<223> OTHER INFORMATION: Pre mir-302a

<400> SEQUENCE: 43
ccaccacuua aacguggaug uacuugcuuu gaaacuaaag aaguaagugc uuccauguuu    60
uggugaugg                                                            69

<210> SEQ ID NO 44
<211> LENGTH: 23
<212> TYPE: RNA
<213> ORGANISM: Homo sapiens
<220> FEATURE:
<221> NAME/KEY: misc_feature
<223> OTHER INFORMATION: miR-302b

<400> SEQUENCE: 44
uaagugcuuc cauguuuuag uag                                            23

<210> SEQ ID NO 45
<211> LENGTH: 73
<212> TYPE: RNA
<213> ORGANISM: Homo sapiens
<220> FEATURE:
<221> NAME/KEY: misc_feature
<223> OTHER INFORMATION: Pre miR-302b

<400> SEQUENCE: 45
gcucccuuca acuuuaacau ggaagugcuu ucgugacuu aaaaguaag ugcuuccaug      60 uuuuaguagg agu                                                       73

<210> SEQ ID NO 46
<211> LENGTH: 23
<212> TYPE: RNA
<213> ORGANISM: Homo sapiens
<220> FEATURE:
<221> NAME/KEY: misc_feature
<223> OTHER INFORMATION: miR-302c

<400> SEQUENCE: 46
uaagugcuuc cauguuucag ugg                                            23

<210> SEQ ID NO 47
<211> LENGTH: 68
<212> TYPE: RNA
<213> ORGANISM: Homo sapiens
<220> FEATURE:
<221> NAME/KEY: misc_feature
<223> OTHER INFORMATION: Pre miR-302c

<400> SEQUENCE: 47
ccuuugcuuu aacauggggg uaccugcugu gugaaacaaa aguaagugcu uccauguuuc    60
aguggagg                                                             68

<210> SEQ ID NO 48
<211> LENGTH: 23
<212> TYPE: RNA
<213> ORGANISM: Homo sapiens
<220> FEATURE:
<221> NAME/KEY: misc_feature
<223> OTHER INFORMATION: Pre miR-302d

<400> SEQUENCE: 48
uaagugcuuc cauguuugag ugu                                            23

```
<210> SEQ ID NO 49
<211> LENGTH: 68
<212> TYPE: RNA
<213> ORGANISM: Homo sapiens
<220> FEATURE:
<221> NAME/KEY: misc_feature
<223> OTHER INFORMATION: Pre miR-302d

<400> SEQUENCE: 49
ccucuacuuu aacauggagg cacuugcugu gacaugacaa aaauaagugc uuccauguuu      60
gagugugg                                                              68

<210> SEQ ID NO 50
<211> LENGTH: 22
<212> TYPE: RNA
<213> ORGANISM: Homo sapiens
<220> FEATURE:
<221> NAME/KEY: misc_feature
<223> OTHER INFORMATION: Pre miR-367

<400> SEQUENCE: 50
aauugcacuu uagcaauggu ga                                              22

<210> SEQ ID NO 51
<211> LENGTH: 68
<212> TYPE: RNA
<213> ORGANISM: Homo sapiens
<220> FEATURE:
<221> NAME/KEY: misc_feature
<223> OTHER INFORMATION: Pre miR-367

<400> SEQUENCE: 51
ccauuacugu ugcuaauaug caacucuguu gaauauaaau uggaauugca cuuuagcaau      60
ggugaugg                                                              68

<210> SEQ ID NO 52
<211> LENGTH: 85
<212> TYPE: RNA
<213> ORGANISM: Homo sapiens
<220> FEATURE:
<221> NAME/KEY: misc_feature
<223> OTHER INFORMATION: Pre miR-124-1

<400> SEQUENCE: 52
aggccucucu cuccguguuc acagcggacc uugauuuaaa uguccauaca auuaaggcac      60
gcggugaaug ccaagaaugg ggcug                                           85

<210> SEQ ID NO 53
<211> LENGTH: 109
<212> TYPE: RNA
<213> ORGANISM: Homo sapiens
<220> FEATURE:
<221> NAME/KEY: misc_feature
<223> OTHER INFORMATION: Pre miR-124-2

<400> SEQUENCE: 53
aucaagauua gaggcucugc ucuccguguu cacagcggac cuugauuuaa ugucauacaa      60
uuaaggcacg cggugaaugc caagagcgga gccuacggcu gcacuugaa                 109

<210> SEQ ID NO 54
<211> LENGTH: 87
<212> TYPE: RNA
<213> ORGANISM: Homo sapiens
<220> FEATURE:
<221> NAME/KEY: misc_feature
```

```
<223> OTHER INFORMATION: Pre miR-124-3

<400> SEQUENCE: 54
ugagggcccc ucugcguguu cacagcggac cuugauuuaa ugucuauaca auuaaggcac      60
gcggugaaug ccaagagagg cgccucc                                         87

<210> SEQ ID NO 55
<211> LENGTH: 89
<212> TYPE: RNA
<213> ORGANISM: Homo sapiens
<220> FEATURE:
<221> NAME/KEY: misc_feature
<223> OTHER INFORMATION: Pre miR-9-1

<400> SEQUENCE: 55 cggggüuggu uguuaucuuu gguuaucuag cuguaugagu ggugüggagu cuucauaaag      60 cuagauaacc gaaaguaaaa auaacccca                                       89

<210> SEQ ID NO 56
<211> LENGTH: 87
<212> TYPE: RNA
<213> ORGANISM: Homo sapiens
<220> FEATURE:
<221> NAME/KEY: misc_feature
<223> OTHER INFORMATION: Pre miR-9-2

<400> SEQUENCE: 56
ggaagcgagu uguuaucuuu gguuaucuag cuguaugagu guauuggucu ucauaaagcu      60
agauaaccga aaguaaaaac uccuuca                                         87

<210> SEQ ID NO 57
<211> LENGTH: 90
<212> TYPE: RNA
<213> ORGANISM: Homo sapiens
<220> FEATURE:
<221> NAME/KEY: misc_feature
<223> OTHER INFORMATION: Pre miR-9-3

<400> SEQUENCE: 57
ggaggcccgu uucucucuuu gguuaucuag cuguaugagu gccacagagc cgucauaaag      60
cuagauaacc gaaaguagaa augauucuca                                      90

<210> SEQ ID NO 58
<211> LENGTH: 84
<212> TYPE: RNA
<213> ORGANISM: Homo sapiens
<220> FEATURE:
<221> NAME/KEY: misc_feature
<223> OTHER INFORMATION: Pre miR-26a2

<400> SEQUENCE: 58
ggcuguggcu ggauucaagu aauccaggau aggcuguuuc caucugugag gccuauucuu      60
gauuacuugu uucuggaggc agcu                                            84

<210> SEQ ID NO 59
<211> LENGTH: 70
<212> TYPE: RNA
<213> ORGANISM: Homo sapiens
<220> FEATURE:
<221> NAME/KEY: misc_feature
<223> OTHER INFORMATION: Pre miR-196

<400> SEQUENCE: 59
```

```
gugaauuagg uaguuucaug uuguugggcc uggguuucug aacacaacaa cauuaaacca    60
cccgauucac                                                          70

<210> SEQ ID NO 60
<211> LENGTH: 84
<212> TYPE: RNA
<213> ORGANISM: Homo sapiens
<220> FEATURE:
<221> NAME/KEY: misc_feature
<223> OTHER INFORMATION: Pre miR-196

<400> SEQUENCE: 60
acuggucggu gauuuaggua guuuccuguu guugggaucc accuuucucu cgacagcacg    60
acacugccuu cauuacuuca guug                                          84

<210> SEQ ID NO 61
<211> LENGTH: 110
<212> TYPE: RNA
<213> ORGANISM: Homo sapiens
<220> FEATURE:
<221> NAME/KEY: misc_feature
<223> OTHER INFORMATION: Pre miR-196

<400> SEQUENCE: 61
ugcucgcuca gcugaucugu ggcuuaggua guuucauguu guugggauug aguuuugaac    60
ucggcaacaa gaaacugccu gaguuacauc agucgguuuu cgucgagggc              110

<210> SEQ ID NO 62
<211> LENGTH: 110
<212> TYPE: RNA
<213> ORGANISM: Homo sapiens
<220> FEATURE:
<221> NAME/KEY: misc_feature
<223> OTHER INFORMATION: Pre miR-10b

<400> SEQUENCE: 62
ccagagguug uaacguuguc uauauauacc cuguagaacc gaauuugugu gguauccgua    60
uagucacaga uucgauucua ggggaauaua uggucgaugc aaaaacuuca              110

<210> SEQ ID NO 63
<211> LENGTH: 84
<212> TYPE: RNA
<213> ORGANISM: Homo sapiens
<220> FEATURE:
<221> NAME/KEY: misc_feature
<223> OTHER INFORMATION: Pre miR-25

<400> SEQUENCE: 63
ggccaguguu gagaggcgga gacuugggca auugcuggac gcugcccugg gcauugcacu    60
ugucucgguc ugacagugcc ggcc                                          84

<210> SEQ ID NO 64
<211> LENGTH: 98
<212> TYPE: RNA
<213> ORGANISM: Homo sapiens
<220> FEATURE:
<221> NAME/KEY: misc_feature
<223> OTHER INFORMATION: pre miR-424

<400> SEQUENCE: 64
cgaggggaua cagcagcaau ucauguuuug aaguguucua aaugguucaa aacgugaggc    60
gcugcuauac ccccucgugg ggaaggguaga aggugggg                          98
```

<210> SEQ ID NO 65
<211> LENGTH: 82
<212> TYPE: RNA
<213> ORGANISM: Homo sapiens
<220> FEATURE:
<221> NAME/KEY: misc_feature
<223> OTHER INFORMATION: Pre-miR 19

<400> SEQUENCE: 65
gcaguccucu guuaguuuug cauaguugca cuacaagaag aauguaguug ugcaaaucua     60
ugcaaaacug augguggccu gc                                              82

<210> SEQ ID NO 66
<211> LENGTH: 87
<212> TYPE: RNA
<213> ORGANISM: Homo sapiens
<220> FEATURE:
<221> NAME/KEY: misc_feature
<223> OTHER INFORMATION: Pre-miR 19

<400> SEQUENCE: 66
cacuguucua ugguuaguuu ugcagguuug cauccagcug ugugauauuc ugcugugcaa     60
auccaugcaa aacugacugu gguagug                                         87

<210> SEQ ID NO 67
<211> LENGTH: 89
<212> TYPE: RNA
<213> ORGANISM: Homo sapiens
<220> FEATURE:
<221> NAME/KEY: misc_feature
<223> OTHER INFORMATION: Pre-miR 149

<400> SEQUENCE: 67
gccggcgccc gagcucuggc uccgugucuu cacucccgug cuuguccgag gagggaggga     60
gggacggggg cugugcuggg gcagcugga                                       89

<210> SEQ ID NO 68
<211> LENGTH: 110
<212> TYPE: RNA
<213> ORGANISM: Homo sapiens
<220> FEATURE:
<221> NAME/KEY: misc_feature
<223> OTHER INFORMATION: Pre-miR 218

<400> SEQUENCE: 68
gugauaaugu agcgagauuu ucuguugugc uugaucuaac caugugguug cgagguauga     60
guaaaacaug guuccgucaa gcaccaugga acgucacgca gcuuucuaca               110

<210> SEQ ID NO 69
<211> LENGTH: 110
<212> TYPE: RNA
<213> ORGANISM: Homo sapiens
<220> FEATURE:
<221> NAME/KEY: misc_feature
<223> OTHER INFORMATION: Pre-miR 218

<400> SEQUENCE: 69
gaccagucgc ugcggggcuu uccuuugugc uugaucuaac caugugguugg aacgauggaa    60 acggaacaug guucugucaa gcaccgcgga aagcaccgug cucuccugca               110

<210> SEQ ID NO 70
<211> LENGTH: 110
<212> TYPE: RNA

```
<213> ORGANISM: Homo sapiens
<220> FEATURE:
<221> NAME/KEY: misc_feature
<223> OTHER INFORMATION: Pre- miR 212

<400> SEQUENCE: 70
cggggcaccc cgcccggaca gcgcgccggc accuuggcuc uagacugcuu acugcccggg      60
ccgcccucag uaacagucuc cagucacggc caccgacgcc uggccccgcc                110

<210> SEQ ID NO 71
<211> LENGTH: 102
<212> TYPE: RNA
<213> ORGANISM: Homo sapiens
<220> FEATURE:
<221> NAME/KEY: misc_feature
<223> OTHER INFORMATION: Pre-miR-137

<400> SEQUENCE: 71
gguccucuga cucucuucgg ugacggguau ucuugggugg auaauacgga uuacguuguu      60
auugcuuaag aauacgcgua gucgaggaga guaccagcgg ca                        102
```